Figure 1:
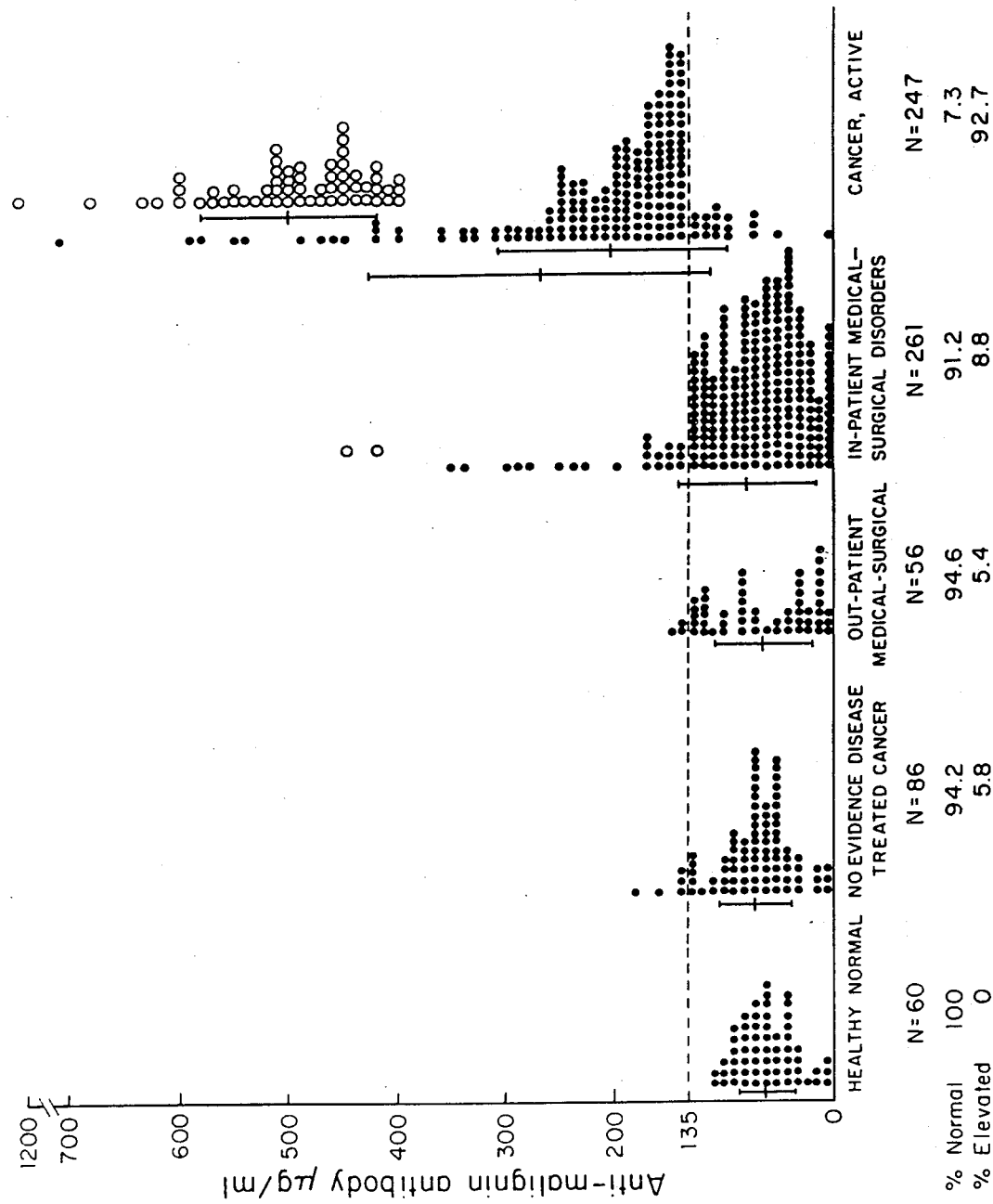

United States Patent [19]

Bogoch

[11] Patent Number: 4,486,538
[45] Date of Patent: Dec. 4, 1984

[54] DETECTION OF MALIGNANT TUMOR CELLS

[76] Inventor: Samuel Bogoch, 46 E. 91st St., New York, N.Y. 10028

[21] Appl. No.: 271,645

[22] Filed: Jun. 8, 1981

Related U.S. Application Data

[63] Continuation-in-part of Ser. No. 922,799, Jul. 7, 1978, Pat. No. 4,298,590, and a continuation-in-part of Ser. No. 553,075, Feb. 25, 1975, abandoned, which is a continuation-in-part of Ser. No. 550,432, Feb. 18, 1975, abandoned, Ser. No. 450,404, Mar. 12, 1974, abandoned, and Ser. No. 385,451, Aug. 3, 1973, abandoned.

[51] Int. Cl.³ .................. C12N 15/00; G01N 33/54; G01N 33/56; A61K 39/395
[52] U.S. Cl. .................. 436/503; 436/504; 436/548; 436/804; 436/813; 436/815; 260/112 R; 435/7; 435/29; 435/70; 435/172.2; 435/240; 424/1.1; 424/9; 424/85; 424/177; 935/103
[58] Field of Search .............. 424/1, 1.5, 9, 12, 85, 424/177; 435/4, 7, 172, 240, 241, 29, 68, 70; 436/548, 518, 519, 813, 503, 504, 547, 804, 815; 260/112 R

[56] References Cited

U.S. PATENT DOCUMENTS

| 4,172,124 | 10/1979 | Koprowski et al. | 424/85 |
| 4,195,017 | 3/1980 | Bogoch | 260/112 R |
| 4,196,186 | 4/1980 | Bogoch | 424/12 |
| 4,196,265 | 4/1980 | Koprowski et al. | 435/2 |
| 4,298,590 | 11/1981 | Bogoch | 424/1 |

OTHER PUBLICATIONS

Chem. Abstracts, vol. 94, p. 261, Abstract 43,717x, Bogoch, S. (1981).
Chem. Abstracts, vol. 94, p. 595, Abstract 137,703s, Bogoch, S. (1981).
Lancet, vol. 2 (8238), pp. 141–142, Bogoch et al., (1981).
Chem. Abstracts, vol. 93(7), Abstract 68,408g, Momoi et al. (1980).
Chem. Abstracts, vol. 88, p. 284, Abstract 18,669b, Bogoch (1978).
Lancet, vol. 1, (8123) p. 987 (1979) Bogoch, S. and Bogoch, E. S.
Chem. Abstracts, vol. 90, Abstract 150,224, Bogoch (1979).
Chem. Abstracts, vol. 93, p. 480, Abstract 130,214d, Bogoch, S. (1980).
Chem. Abstracts, vol. 94(23), Abstract 190,153p, (1981), Sikora et al.
Cancer Research, vol. 41(10) pp. 4031–4038 (1981) Knowles A. F. et al.

Primary Examiner—Benjamin R. Padgett
Assistant Examiner—M. Moskowitz

[57] ABSTRACT

Described herein is the production of two products which are distinct species of anti-malignin antibody, and the production of three artificially produced species of cell each of which has the distinguishing characteristic of manufacturing either one or both species of anti-malignin antibody. These anti-malignin products are useful to detect the presence of cancerous or malignant tumor cells. These anti-malignin products attach preferentially to cancerous or malignant tumor cells in cell collections in vitro or in vivo and thus can be detected by any attached visible or other signal emitter. This preferential attachment to malignant tumor cells also makes these products useful for metabolic and therapeutic purposes.

21 Claims, 2 Drawing Figures

DETECTION OF MALIGNANT TUMOR CELLS

CROSS REFERENCES TO OTHER APPLICATIONS

This application is a Continuation-in-Part of my allowed application (C. M. Nucker, Art Unit 223), Ser. No. 922,799 filed July 7, 1978, entitled DETECTION OF MALIGNANT TUMOR CELLS, now U.S. Pat. No. 4,298,590 issued 11/3/81 and now abandoned application Ser. No. 553,075 filed 02/28/75, which in turn is a Continuation-in-Part of each of my applications Ser. No. 550,432, filed Feb. 18, 1975, now abandoned, entitled RECOGNINS AND THEIR CHEMORECIPROCALS; Ser. No. 450,404, filed Mar. 12, 1974, now abandoned; and Ser. No. 385,451, filed Aug. 3, 1973, now abandoned.

THE INVENTION

This invention relates to (1) the production of two products which are distinct species of anti-malignin antibody; and (2) the production of three artificially-produced species of cell, each of which has the distinguishing characteristic of manufacturing either one or both species of anti-malignin antibody; whereby the above products, both the antibodies themselves and the cells which produce them, are useful for diagnostic, metabolic and therapeutic purposes.

The process of fusion of cell hybrids, is now a routinely used and accepted procedure in the art (Monoclonal Antibodies, Cesar Milstein, Scientific American, May 1980, pp. 66–74). The producton of antibodies by the injection of tumor cells into animals has also been a common procedure in the art for many years. A U.S. Pat. No. 4,172,124, Hillary Koprowski and Carlo M. Croce) relates to a method of producing antibodies to whole tumor cells, the critical first step of which is the injection into an animal of whole cells from various tumors, and therefore differs from the present invention which does not utilize the injection of whole cells but rather requires the use of a specific polypeptide composition, Malignin, the subject of my U.S. Pat. Nos. 4,195,017 and 4,196,186, to produce specific species of a specific antibody, anti-malignin antibody.

Malignin was earlier used to produce anti-malignin antibody, also a subject of my earlier patents above. But whereas these patents describe the production of polyclonal anti-malignin antibody in mammals, the anti-malignin antibodies of the present invention are monoclonal, and are the products of single artificially produced cells. In addition to a different mode of production, as will be set forth herein, the present monoclonal antibodies have unique properties, and should therefore be uniquely referred to in order to distinguish them from the anti-malignin antibody which is polyclonal, is produced in mammals, and has different properties.

The artificially produced cell lines themselves, which have been produced by the present invention, which have the ability to produce Monoclonal Anti-Malignin Antibodies, are also themselves unique and novel in that a single (monoclonal) line or type of cell has been produced artificially with the patented product Malignin, and perpetuated in vitro, which has the ability to produce Monoclonal anti-Malignin Antibody. Further, this novel cell line can produce Monoclonal Anti-Malignin Antibody in perpetuity and in any quantities desired. These new artificial cells are therefore herewith designated Monoclonal Anti-Malignin Antibody-Producing-Cells. These new cells have immediate utilities related to the patented utilities of their product antibody, i.e. diagnostic and therapeutic. Thus the earlier patents make clear both in their specifications and their examples the use of the antibody diagnostically to identify the presence of either the antigen Malignin, or any cells which contain Malignin, or to treat therapeutically (i.e. destroy) such cells, i.e. malignant or cancerous cells by the specific reaction of anti-malignin antibody with its specific antigen malignin whether in solution or fixed in cells. (See examples 11, 11A, 12 for the use of the antibody to stain cancer cells specifically in immunofluorescence, and see example 13 for the use of the antibody to identify or attach specifically to cancer cells carrying either a signal-emitter for identification and localization of the cancer cells in the body, or carrying an anti-cancer drug or chemical to be concentrated in the cancer cell for its destruction, as well as examples 16, 17 where the antibody alone is used to treat (destroy) cancer cells.)

From the earliest production by the inventor of anti-malignin antibody (Issued U.S. Pat. Nos. 4,195,017 and 4,196,186) two constituent species of the antibody were recognized: (1) Fast Target-attaching-globulin (F-TAG), which combined rapidly in vitro, within 10 minutes, with its specific immobilized antigen malignin; and (2) Slow Target-attaching-globulin (S-TAG), which combined slowly in vitro, within 2 hours, with its specific immobilized antigen malignin (see Examples 10,10A). Both S-TAG and F-TAG were produced from blood serum, and the determination of their concentration in serum of individuals became the basis of the cancer diagnostic test which is the subject of issued U.S. Pat. No. 4,196,186. The method of production of each species however never yielded either one completely free of the other. The present invention is a marked improvement since it describes the production of a unique novel cell line which produces only the S-TAG species, one cell line which produces only the F-TAG species, and one cell line which produces both species.

As summarized above, the ability of the previous polyclonal anti-malignin antibody, which contained both species, to destroy cancer cells specifically (cytotoxicity) was described in U.S. Pat. No. 4,195,017. In the present invention, it has been found that the single species of monoclonal antibody product produced here for the first time S-TAG, Monoclonal Anti-Malignin Antibody—Slow (MAMA-S), attaches preferentially to cancer cells but does not destroy them. Also, the single species of monoclonal antibody product here produced for the first time for F-TAG, Monoclonal Anti-Malignin Antibody—Fast (MAMA-F) attaches preferentially to cancer cells but does not destroy them. The species of combined antibody here produced for the first time by monoclonal producer cells, designated MAMA-FS, as well as an artificial mixure of the two antibodies MAMA-S and MAMA-F, attach preferentially to cancer cells and destroy them. The separation of the attachment from the destruction functions of the species of the anti-malignin antibody described in this invention has important applications in the separate uses of the antibody now possible for diagnosis on the one hand and for treatment (destruction of cancer cells) on the other. The respective novel producer cells are designated MAMA-A Producer, MAMA-F Producer, and MAMA-FS Producer, each being uniquely characterized by its specific antibody product.

The careful study over the past seven years of the possible relation of the concentration of anti-malignin antibody in the serum of individual patients suffering cancer has provided unequivocal data presented in this application (Example 10A) that patients who survive longer, 13 to 46 months, have higher levels of antibody than those who died in one year. Of all patients with low levels of antibody (83.3%) were dead within one year (mean 4.4±3.5 mos.). This clear association of survival with increased amounts of anti-malignin antibody give new significance to the therapeutic utility of this antibody. Whereas the therapeutic use of anti-malignin antibody was clearly demonstrated in the earlier patents of this series (cytotoxicity to cancer cells) it was not known how much difference the availability of extra antibody would make to the balance between cancer and normal cells, that is, how important this therapy might be to the survival of the cancer patient. The present clinical study makes it clear that the level of anti-malignin antibody available appears to be clearly associated with survival.

The new inventions described in this application whereby the patented product malignin has been used to produce novel cells which themselves manufacture in perpetuity in virtually limitless quantities specific preferentially-attaching and cancer cell destroying anti-malignin antibodies therefore acquire added significance as novel therapeutic anti-cancer products.

These novel cells, which could be and have been produced artificially only through contact with the patented product malignin, carry the permanent instruction in their genetic apparatus to manufacture the particular product antibody indefinitely. They also carry the instruction to continue to divide indefinitely. Both these instructions are seen to be carried out in the Examples herein. It follows to those familiar with the art that the particular cellular constituents which carry this genetic information can now be isolated and induced to perform their particular functions in the antibody manufacture in vitro should this be particularly useful. Fox example, should there be an efficiency, cost or other advantage to doing so, the nucleic acid of the producer cell which carries the specific information for manufacturing the particular monoclonal anti-malignin antibody produced by that particular cell can now be removed and isolated from the other cellular constituents and inserted into another type of cell, for example, bacterial, which might divide more quickly, be less susceptible to contamination during bulk manufacture or less costly to maintain in the laboratory continuously. This is only one example of the application of any method practiced by the art which may only now be used since the unique cell, MAMA-S, MAMA-F or MAMA-FS, produced by the unique product malignin, has been produced and is self-perpetuating as described in the present invention.

Anti-malignin antibody reacts specifically immunologically not only with the antigen malignin, but also with the closely structurally related products such as Astrocytin, Recognin L and Recognin M. This present invention therefore continues to be directed to the novel group of compounds, herein termed Recognins. Recognins are made by treating tumor cells or artificial cancer cells and separately the desired products. The Recognins may be used to prepare their Chemoreciprocals, i.e., by contacting the Recognins or the Recognins on a support with body fluids. These Chemoreciprocals are useful for diagnostic and therapeutic purposes, i.e., for diagnosing and treating cancers.

One of the Recognins of the present invention is Astrocytin. Astrocytin is produced from brain tumor tissue, preferably brain glioma tumor tissue. Protein fractions containing the Astrocytin precursor are first extracted from the tissue. A preferred method of accomplishing the extraction is to treat the tissue with a neutral buffer under conditions of homogenization or other techniques to disrupt the cells and tissues in order to solubilize protein fractions which contain the Astrocytin precursor.

At this point, the Astrocytin precursor is still bound to many large molecular weight substances including protein, glycoproteins, lipoproteins, nucleic acids, nucleo-proteins, etc. The solubilized proteins are then separated from the resultant tissue extract. The extract solution from the tissue is then clarified to remove insoluble particles. The low molecular weight contaminants are then removed from the resultant solution, by a perevaporation concentration technique. The solution which is obtained is then treated to cleave Astrocytin precursor from other contaminants in order to obtain the protein fraction having a pK range between 1 and 4. Thus, for example, the solution is placed on a chromatographic column and eluted with increasing acidic solvents. All of the fractions which are eluted in the neutral or acid range down to pK 4 are discarded and those fractions with pK range 1-4 are collected. The eluate is then treated to obtain a product having a molecular weight of about 8,000. This is accomplished, for example, by first filtering the material to remove low-molecular-weight substances, i.e., those below 1,000 molecular weight, and filtering again to remove those above 25,000. The fraction having a molecular weight between 1,000 and 25,000 is then further treated, i.e., by thin layer gel (TLG) chromatography, to obtain Astrocytin.

Thus Astrocytin may be produced by extracting brain glioma tumor tissue with a neutral buffer, by repeated homogenization and high speed centrifugation, separating from the resulting extract the fraction having a pK range of from about 1 to 4, separating from said fraction the substances having a high molecular weight, i.e., up to about 230,000, and isolating therefrom the product Astrocytin having a molecular weight of about 8,000.

The product Astrocytin prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length of 280 m$\mu$ and having a molecular weight of about 8,000.

Astrocytin is also characterized by having a very high percentage of residues of glutamic acid and aspartic acid and a very high ratio of these acids to histidine. A further analysis of Astrocytin is provided below.

In a manner similar to that described above, another Recognin, called Malignin, is produced from artificial cancer cells, i.e., cancer cells grown in vitro. Malignin has a molecular weight of about 10,000 and similar but distinct amino acid residue composition to Astrocytin, i.e., high amounts of glutaminic acid and aspartic acid and high ratios of these acids to histidine. A further analysis of Malignin is provided below.

Thus, Malignin can be produced by extracting artificial cancer cells grown in culture with a neutral buffer by repeated homogenization and high speed centrifugation, separating from the resulting extract the fraction having a pK range of about 1 to 4, separating from said fraction the substances having a high molecular weight, i.e. up to about 230,000, and isolating therefrom the product having a molecular weight of about 10,000.

Malignin prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length of 280 m$\mu$ and having a molecular weight of about 10,000.

Recognins are further characterized by being capable of complexing with bromoacetylcellulose to form bromoacetyl-cellulose-Recognin and producing the specific antibodies Anti-Recognin upon injection into mammals, said Anti-Recognin being toxic to brain tumor cells in vitro and producing fluorescence of glioma cells when coupled with fluorescein, as described in further detail below.

Recognins, such as Astrocytin, Malignin and similar substances are useful as products which may be introduced into a biological system to reduce foreign reactions, such as by coating a material with a Recognin. A further example may be to introduce a Recognin in order to produce the Chemoreciprocals in the biological system. They may also be used nutritionally to encourage the growth of a particular biological system of which they are a part. A further utility of Recognin is the production of Target reagents which comprise the complexes of the Recognin with a carrier to facilitate its applicability in biological systems. Thus, for example, the complex conveys the physical-chemical characteristics of the Recognin itself. The carrier should be selected from those which form a complex with the Recognin and which are substantially biologically inert.

Any substance known in the art which will form a stable complex with polypeptides or proteins may be useful for complexing with the Recognin. An example is a cellulose-based material, such as bromoacetyl-cellulose. In addition to being inert to the biological system, the carrier should be one that does not alter the specific physical-chemical properties of the Recognin which are useful for the purposes set forth herein.

The complexes of the Recognin and its carrier are useful for producing, separating and identifying its chemoreciprocal in any biological system with which it is brought into contact. The Recognin-carrier complex is also useful for stimulating the production of its chemoreciprocal precursor in any biological system into which it is introduced.

One class of Chemoreciprocals are the anti-Recognins, i.e., anti-Astrocytin and anti-Malignin. These may be made by injecting the Recognin into a biological system. An immunologically effective dose of Recognin is brought into contact with bodily tissues or fluids in a manner which induces an antibody response in accordance with techniques known in the art for producing antibodies. The anti-Recognins may be used for the delivery of materials such as diagnostic, nutritional and therapeutic agents to specific cells or sites in a biological system which comprises introducing said agent in complexed form with the anti-Recognin into the biological system. The anti-Recognins are also useful for diagnosing the presence of tumor cells in a histology section, by applying the Anti-Recognin conjugated with a labeling substance such as dyes and radio-active substances, to said section, whereby staining or radioactive labeling occurs only with tumor cells. Yet another use for anti-Recognins is for increasing the yield of other useful Chemoreciprocal products (such as TAG, described below) from a mammal which comprises injecting an immunologically effective dose of Recognin into the mammal, or other biological system.

Another class of Chemoreciprocals is Target reagents complexed with their chemoreciprocals. For example, the Target product of Astrocytin complexed with a carrier such as bromoacetylcellulose is brought into contact with anti-Astrocytin. This type of compound may be complexed with and used for the delivery of diagnostic, nutritional and therapeutic agents to specific cells or sites in a biological system. These compounds may also be used for purification procedures. For example, Anti-Astrocytin may be made by the decomplexing of Bromoacetylcellulose-Astrocytin-Anti-Astrocytin by hydrolytic treatment with an acid or proteinase enzyme. Target reagents are also useful for increasing the amount of TAG products (described below) in a biological system, such as by bringing an immunologically effective dose of Target into contact with bodily tissues or fluids.

Additional Chemoreciprocals are TAG reagents (e.g., Target-Attaching-Globulins). The TAG products are produced by bringing Target reagents into contact with body fluids for varying periods of time to form a complex and cleaving TAG therefrom. Two useful embodiments are S-TAG and F-TAG.

A process for producing S-TAG (Slow-Target-Attaching-Globulin) comprises reacting blood serum or other body fluid with Target (i.e., Bromoacetylcellulose-Malignin) for approximately two hours or more at a low temperature, e.g., about 4° C., and cleaving S-TAG from the resulting material, e.g., with dilute acid for approximately two hours at a temperature of about 37° C. The product S-TAG prepared in accordance with this process is characterized by being soluble in aqueous buffered solutions, forming a single line precipitate with its corresponding Recognin in Ouchterlony gel diffusion tests, being Non-dialyzable in cellophane membranes, being retained by millipore filters which retain molecules over 10,000 molecular weight, having molecular weights in different states of aggregation as determined by thin layer gel chromatography of approximately 50,000, and multiples thereof into the macroglobulin range and having a spectrophotometer absorption peak wave length of 280 m$\mu$.

A process for producing F-TAG (Fast-Target-Attaching-Globulin) comprises reacting blood serum or other body fluid with Target (i.e., Bromoacetylcellulose-Malignin) for approximately 10 minutes at a low temperature, e.g., about 4° C., and cleaving F-TAG from the resulting material, e.g., with dilute acid for approximately two hours at a temperature of about 37° C. The product F-TAG prepared in accordance with this process is characterized by being soluble an aqueous buffered solutions, forming a single line precipitate with its corresponding Recognin in Ouchterlony gel diffusion tests, being non-dialyzable in cellophane membranes, being retained by millipore filters which retain molecules over 25,000 molecular weight, having molecular weights in different states of aggregation as determined by thin layer gel chromatography of approximately 50,000, and multiples thereof into the macroglobulin range and having a spectrophotometer absorption peak wave length of 280 mµ.

TAG products are useful for detecting cancer tumors in living mammals by determining the concentration of S-TAG and F-TAG produced by a known volume of the mammal's blood serum or other body fluid and correlating this concentration with amounts determined to be indicative of cancer. TAG products are also useful for diagnosing the presence of tumor cells in a histology section, which comprises applying TAG conjugated with a labeling substance such as dyes and radioactive substances, to said section, whereby staining or radioactive labeling occurs only with tummor cells. TAG products additionally have been found to be cytotoxic to tumor cells. TAG products are also useful for directing the delivery of diagnostic, nutritional and therapeutic agents to specific cells or sites by introducing said agents in complexed form with the TAG product.

Normal cell division in plants or animals is restricted or inhibited when the cells come to occupy fully a particular space. The mechanisms (a) by which normal cells "recognize" that they have filled the space available to them, and (b) by which the operation of this recognition mechanism in turn inhibits cell division, have both been unknown. The inventor has produced a group of compounds whose precursors are increased in concentration when normal recognition and learning occur, and which relate to recognition and learning on particles and cells, and with the connection of cells to each other. These compounds are termed RECOGNINS by the inventor. By attempting to produce these compounds from normal cancer cells, the inventor has discovered that they are absent as such, and that changes in their molecular structure have occurred at the same time that the cancer cells have lost their ability (a) to recognize that they have filled their normal volume, and/or (b) to stop dividing when they have filled their normal volume.

The inventor has discovered novel compounds and methods for producing such compounds. These new compounds are termed RECOGNINS by the inventor. RECOGNINS are novel compounds which have physicochemical characteristics which mimic those confugurations characteristic of cancer cells in terms of their failure to recognize and stop cell division. The use of RECOGNINS goes beyond insight into the cancer mechanism, for immediate products and methods are thereby provided which are useful in the diagnosis and treatment of cancer, and for its prevention.

I have discovered methods by which artificially cultured cells can be used to produce MALIGNINS for the first time. One advantage of the methods disclosed herein is that MALIGNINS and new products from them can now be manufactured efficiently in virtually limitless quantities.

This invention transcends the field of cancer research and is immediately applicable to any and all biological systems in which it is desired to influence all growth and metabolism. Thus by the manufacture of the particular compound or compounds of appropriate cell type in artificial culture, and the further manufacture of products from these substances, specific influence may for the first time be brought to bear on any tissue, cell, cell organelle, sub-organelle molecular or molecular aggregate in any living system. Thus specific nutritional influences at critical times in development, specific diagnostic, preventative and treatment methods, and the construction of artificial bioelectrical systems (as in tissue or organ transplants) can all be affected for the first time. These artificial bioelectrical systems can now be made to bear the characteristics of the specific RECOGNIN, MALIGNIN or their CHEMORECIPROCALS of the normal tissue or component which they will neighbor and thus avoid being "recognized" as "foreign" and thus avoid the reactions to alien substances, including rejection.

Another aspect of this invention is the production of a valuable specific antibody-like product (Anti-Astrocytin) to a specific brain product (Astrocytin), permitting the use of this antibody-like product to specifically complex with and, as a specific delivery vehicle to, specific points in the nervous system of all species. MALIGNINS and ASTROCYTIN are RECOGNINS.

Still another aspect of this invention is the production from biological fluids of two new products, TARGET-ATTACHING-GLOBULINS (TAG), which are so named because they are produced by two reactions, the first reacting biological fluids with a synthetic complex containing physicochemical configurations which mimic those of the MALIGNINS and called TARGET, the second, cleaving the specific TAG from the complex, and by the measure of the TAG so produced obtaining a quantitative indication from the biological fluids of living organisms whether these is present a tumorin that organism; hence a diagnostic test for tumors. Because TAG products and ANTI-MALIGNIN are physicochemically complimentary to MALIGNINS, they are termed CHEMORECIPROCALS.

I have further discovered that two quantitatively and qualitatively distinct TAG products can be produced depending upon the time permitted for the reaction of serum with the specific TARGET reagent used, and depending upon the time permitted for the cleavage of the product which has been complexed.

After examining the amounts of these products which could be produced from a number of different individuals with brain tumors and various other medical disorders, as well as in those with no apparent disease process, it became apparent that the amounts of these two new products which could be produced in a given individual was indicative of whether that individual had a malignant tumor, hence a serum diagnostic test for malignant tumors, the first to my knowledge.

The utility of these new products, in addition to their use to diagnose from serum and other biological fluids the presence of brain and other tumors, is illustrated by the demonstration that TAG and anti-RECOGNIN compounds attach to glial tumor cells preferentially in histological sections of brain tumor and surrounding tissue removed at surgery of the brain tumor. This preferential labelling by TAG and Anti-RECOGNINS of tumor cells is demonstrated through standard immunofluorescent techniques. Thus a new method is also available for determining through histological examination with a new degree of certainty whether tumor cells are present in the tissue removed, and whether these tumor cells have penetrated to the very edges of the tissue removed indicating the likelihood that tumor still remains in the brain or other organ, or that tumor cells are absent from the periphery of the tissue removed, indicating the possibility that all of the tumor has been removed from the brain or other organ. In addition, TAG and Anti-RECOGNINS produced as described have been found to be cytotoxic for glioma brain tumor cells grown in tissue culture in vitro. This high affinity for tumor cells in another medium, here grown in tissue culture, is further evidence of the specific-coupling potential of the new product TAG, and explains the adoption of the name TARGET-ATTACHING-GLOBULINS (TAG) as do TAG's properties in regard to the synthetic product TARGET, and to tumor cells in histological section. Further, the cytotoxicity of TAG and anti-RECOGNINS for tumor cells provides an additional new diagnostic test for serum of patients who are suspected of suffering from a tumor. Thus, for example, the serum or other body fluid of these patients is reacted with TARGET to produce TAG and the product TAG is tested in tissue culture growths of tumor cells for cytotoxicity. Both the concentration of TAG and the degree of cytotoxicity manifested by the TAG which can be produced from a given individual's serum may be not only diagnostic but also of value in tracing the course of the disorder preoperatively and postoperatively in a given patient. Coupling of radioactive and dye tracers to TAG provides new TAG products which are useful in vivo in the diagnosis of tumors and in their exact localization. Thus the injection of suitably labelled TAG either intraarterially or intravenously, into the cerebrospinal fluid, or directly into brain tissue or its cavities, permits the demonstration by radioactive means, or by visualization of the coupled dye, of the presence of a brain tumor, for it is only to the tumor cells that the TAG specifically attached. Further, this method permits the precise visualization of the location of the brain tumor. This can be seen to be an improvement of this in vivo diagnostic method using anti-ASTROCYTIN produced in rabbit blood to label the brain tumor, because the use of TAG produced from human serum avoids the possibility of foreign protein reactions. Since TAG and anti-RECOGNINS have the chemical specificity which permits preferential attachment to ASTROCYTIN precursor containing tumor cells both in vitro and in vivo, these products may also be used therapeutically, as well as diagnostically, when coupled, e.g., with radioactive, proton capture agents, or other toxic physical or chemical agents, so that these toxic substances may be localized preferentially through these compounds' specificity of attachment in the tumor cells as compared to their neighboring normal cells. This selectivity is universally recognized as the crucial, or at least one crucial factor for achieving effective chemical or physical therapy of tumors, and a factor which has hitherto not been achieved. Thus TAG has demonstrated efficacy in attaching preferentially to the tumor cells, and has the properties as a new therapeutic product for these reasons.

In the serum of patients with malignant tumors, as will be seen in the examples below, one type of TAG, SLOW-TAG (S-TAG) as distinguished from FAST-TAG (F-TAG), can be produced in relatively greater amounts from a give volume of serum than in patients without such tumors. This suggests that either one of TAG's naturally occuring precursors (P-TAG) is increased in concentration or that other factors exist which favor the relative in vitro production of S-TAG over F-TAG.

The possible relationship of the function of the actual synthetic products TARGET and TAG to their precursors, and in turn functions of postulated but not demonstrated cell "antigens" and circulating "antibodies" to them which may exist in vivo has yet to be elucidated. Thus for example, in antibody-like fashion, F-TAG and S-TAG produce single discrete lines of reaction with ASTROCYTIN in Oucherlony get diffusion, and the injection of TARGET in rabbits induces an increase in the yield of TAG products from rabbit serum after reacting with TARGET. The finding that there may be a normal level of a precursor resembling circulating antibody to a cell antigen which is hidden in the non-dividing cell raises a question as to the possible function of the pair. It is here proposed that TAG precursor (P-TAG) and TARGET-like substances exist in vivo which function in the control of cell proliferation and cell death. Thus, for example, the exposure of a cell constituent which normally is not directly exposed to serum proteins may occur during cell division. The exposure of this cell constituent could result in that constituent becoming converted to a TARGET-like substance to which the attachment of a P-TAG like molecules from serum may then occur, which would stimulate cell division or inhibit it. Alternatively, a non-dividing cell which is injured or malfunctioning may expose a TARGET-like substance to which the attachment of P-TAG like molecules may be reparative. However, under certain cell conditions the attachment of P-TAG like molecules may induce the destruction of the cell (e.g. ANTI-GLIOMA-TAG synthetically produced as here described is markedly cytotoxic to glioma tumor cells growing in tissue culture). This could thus represent a mirror of a normal mechanism for the control of cell division, and for either the repair or the removal of individual cells in the body throughout the life of the organism. If the exposure of cell constituents is abnormally increased so that abnormally large amounts of cell TARGET-like substances are formed, as may occur in rapidly dividing cancer cells such as in brain gliomas, an increase in the concentration of one type of serum P-TAG relative to another may be induced.

Whatever the actual function of the precursors, the increase in the relative amount of predominately one type of TAG, SLOW-TAG (S-TAG) which can be produced in vitro by the methods here described from the serum of patients with malignant tumors is the basis of the serum diagnostic test described in the examples which follow.

The ability to produce specific monoclonal species for S-TAG and F-TAG by means of new artificially produced cells as herein described, has permitted the separation of certain functions of these TAG molecules, which were previously not separable because they were mixed in the polyclonal form of their production. Thus whereas the earlier TAG products had both the properties of preferential attachment to malignant cells and the cytotoxic property wherein the malignant cell is destroyed, the presently described monoclonal forms of TAG, MAMA-A and MAMA-B, each demonstrates preferential attachment and thus specific fluorescence with malignant cells but are not cytotoxic; whereas a mixture of MAMA-A and MAMA-B produces both fluorescence and cytotoxicity. The separation of diagnositc and therapeutic uses is thus possible for the first time.

The following examples illustrate the invention.

EXAMPLE I

Production of Crude ASTROCYTIN-Precursor-Containing Fraction

Human brain glioma tumor tissue, removed at surgery, is dissected free as possible of surface blood vessels and normal brain tissue. For a typical amount of dissected tumor tissue of 11 grams, the tissue is weighed into six 1.5 g. and two 1.0 g. aliquots. Each aliquot is then treated as follows.

Each aliquot is homogenized in neutral buffer solution by sonification or other mechanical means. For example, each aliquot is homogenized in 100 cc per g. of tissue of 0.005 M phosphate buffer solution, pH 7, in a Waring blender. Homogenization should be done in the cold to prevent denaturation of proteins. For example, the blender should be precooled in a cold room at 0°–5° C. and operated for about only three minutes.

The homogenate is then centrifuged for clarification, for example at 80,000 times gravity for 30 minutes in a refrigerated ultracentrifuge. The soluble supernatant is decanted and kept in the cold. The insoluble residue is rehomogenized with a further 100 cc of neutral buffer and centrifuged as before, and the second soluble extract combined with the first. Best yields are obtained when this procedure of homogenization and centrifugation is repeated until less than 50 micrograms of protein per ml. of solution are obtained in the supernate. With most tissues this is accomplished by the fifth extraction.

The solutions thus obtained are combined and concentrated by perevaporation with subsequent dialysis, as by dialysis against 0.005 M phosphate buffer in the cold to produce a volume of 15 ml. The volume of this solution is noted, an aliquot is taken for total protein analysis, and the remainder is fractionated to obtain the protein fraction having a pK range between 1 and 4. The preferred method of fractionation is chromatography as follows.

The solution is fractionated in the cold room (4° C.) on a DEAE cellulose (Cellex-D) column 2.5×11.0 cm., which has been equilibrated with 0.005 M sodium phosphate buffer. Stepwise eluting solvent changes are made with the following solvents (solutions): Solution (1) 4.04 g. $NaH_2PO_4$ and 6.50 g. $Na_2HPO_4$ are dissolved in 15 liters of distilled $H_2O$ (0.005 molar, pH 7); Solution (2) 8.57 g. $NaH_2PO_4$ is dissolved in 2480 ml. of distilled $H_2O$; Solution (3) 17.1 g. of $NaH_2PO_4$ is dissolved in 2480 ml. of distilled $H_2O$, (0.05 molar, pH 4.7); Solution (4) 59.65 g. of $NaH_2PO_4$ is dissolved in 2470 ml. distilled $H_2O$ (0.175 molar); Solution (5) 101.6 g. of $NaH_2PO_4$ is dissolved in 2455 ml. distilled $H_2O$ (0.3 molar, pH 4.3; Solution (6) 340.2 g. of $NaH_2PO_4$ is dissolved in 2465 ml. of distilled $H_2O$ (1.0 molar, pH 4.1); Solution (7) 283.64 g. of 80% phosphoric acid ($H_3PO_4$) is made up in 2460 ml. of distilled $H_2O$ (1.0 molar, pH 1.0).

Add nervous tissue extract, 6 to 10 ml. volume. Let it pass into column. Then overlay with Solution (1) and attach a reservoir of 300 ml. of Solution (1) to drip by gravity onto the column. Three ml. aliquots of effluant are collected by means of an automatic fraction collector. The subsequent eluting solutions are exchanged stepwise at the following elution tube numbers. Solution (2): at tube 88, bring solution on column to top of resin, then overlay and attach reservoir of 50 ml. of Solution (2); Solution (2): at tube 98, bring solution of column to top of resin, then overlay and attach reservoir of 75 ml. of Solution (3); Solution (4): at tube 114, bring solution on column to top of resin, then overlay and attach reservoir of 150 ml. of Solution (4); Solution (5): at tube 155, bring solution on column to top of resin, the n overlay and attach reservoir of 125 ml. of Solution (5); Solution (6):at tube 187, bring solution on column to top of resin, then overlay and attach reservoir of 175 ml. of Solution (7); continue eluting until at tube 260, elution is complete. Use freshly prepared resin for every new volume of tissue extract. Each effluent tube is quantitatively analyzed for protein. The eluates in the tube numbers 212 to 230 are combined, and contain the crude products from which ASTROCYTIN will be produced.

While data has been published on this crude material, called fraction 10B in the past, (*Protein Metabolism of the Nervous System*, pp. 555–569 (Plenum Press, 1970); Journal of Neurosurgery, Vol. 33, pp. 281–286 (September, 1970) the cleavage from fraction 10B can be prepared as a product in amounts between 0.1 and 10 mg. per gm. of original fresh nervous system tissue from which it was obtained. In addition to an ASTROCYTIN-precursor it contains varying amounts of covalently bound carbohydrate residues including a number of hexoses, namely glucose, galatose, mannose; hexosamines, including glucosamine, galatosamine and mannosamine; and occasionally other sugars, such as fucose, ribose and perhaps rhamnose. It also contains large molecular weight protein products, several lipids and nucleic acids.

EXAMPLE 2

Production of Purified ASTROCYTIN FROM Crude ASTROCYTIN-Prescursor-Containing Fraction The ASTROCYTIN-Precursor-Containing fraction is further isolated from contaminants. In the preferred embodiment, the material from Example 1 is chromatograted on Sephadex G-50 resin with a typical column of 40 cm. long, 2.5 cm. diameter, and 196 ml. volume. The pressure used is 40 mm. Hg; the flow rate is 35 ml. per hour, and the buffer is 0.05molar phosphate buffer solution, pH 7.2. The first (flow-through) peak contains ASTROCYTIN-Precursor together with impurities, whereas subsequent peaks contain only impurities.

In the preferred embodiment, the products in the above first flow-through peak are then concentrated on Sephadex G-15; then passed onto a column of Cellex-D with the same solutions, (1) through (7) as Example 1, and the same elution steps as performed in Example 1. The product ASTROCYTIN is present as a sharp peak in the same tubes (numbers 212–230) as before, thus maintaining the behavior on Cellex-D chromatography without the presence of a large number of contaminants.

Low molecular weight contaminants may then be removed by techniques known to the art, such as millipore disc filtration. In the preferred method, to product ASTROCYTIN is freed of salt and other small molecular weight contaminants by filtration through Millipore Pellicon Disc No. 1000, 13 mm., which retains substances of molecular weight greater than 1000 and permits to pass through those of molecular weight less than 1000. The product ASTROCYTIN remains on the Pellicon Disc, and is recovered from it be washing with Solution (1) of Example 1.

ASTROCYTIN is then obtained by isolating the compound having a molecular weight of about 8000 from the above solution. A preferred method uses thin layer gel (TLG) chromatograph as follows:

The apparatus used in the commercialy available one designed by Bochringer Mannheim GmbH; Pharamacia Fine Chemicals and CAMAG (Switzerland). The resin 2.5 g. of Sephadex g-200 superfine is prepared in 85 ml. of 0.5 M. NaCl in 0.02 M. $Na_2HPO_4KH_2PO_4$ Phosphate Buffer pH 6.8 (6.6–7.0). Allow to swell two or three days at room temperature with occasional gentle mixing. (Magnetic and other stirrers should not be used.) The swollen gel is stabilized for three weeks at refrigerator temperature; however, bacterial and fungal growth may interfere with the swollen gel. If the gel is to be kept for longer periods of time, a small amount of a bacteriostatic agent should be added (sodium azide 0.02%) 2.5 g. of dry gel are used to make two 20×20 cm. glass plates of 0.5 mm. thick. The plates are either allowed to dry at room temperature for 10 minutes and transferred to a moist chamber where they can be stored for about two weeks, or they are used immediately after appropriate pre-equilibration. (Usually during the night for a minimum of 12 hours.) The main function of equilibration is to normalize the ratio between the stationary and mobile phase volumes. With the pre-equilibrated plates in a horizontal position, substances to be determined are applied with micropipettes as spots or as a streak at the start line. 10 ml. to 20 ml. of 0.2-2% protein solution is placed on the edge of a microscopic cover slide (18×18 mm.) and held against the gel surface. In a few seconds the solution will soak into the gel. All samples are first prepared on the cover slides and then quickly applied. If not enough material is used, it is difficult to locate individual spots after separation. If too much material is applied no defined separation occurs. The samples are diluted with buffer for easier handling and the separation of samples is carried in a descending technique with the plate at an angle of 22°. The flow rate of about 1-2 cm/hour is most suitable. Marker substances (such as cytochrome C, haemoglobin, myoglobin or bromophenol Blue labeled albumin) are applied at different positions across the plate to give a check on possible variation of flow across the plate and also to serve as reference proteins for calculation of relative distance (mobility) of unknowns. After application of samples, the plates are replaced in the apparatus and the paper wick pushed slightly downwards to ensure good contact with the gel layer. The paper wick must not drip. Excess moisture is wiped off. The liquid solvent in the reservoir is kept constant at 1 cm. from the upper end of the vessel. The runs are usually completed in 4 to 7 hours depending on the progress of separation. With colored substances separation follows directly. The separated spots of protein are easily made visible by transferring them to a paper sheet replica of TLG plate after the chromatographic separation has been completed, and by staining them on the prewashed methanol+$H_2O$+acetic acid—90:5:5, for 48 hours. The paper sheet is 3 mm. filter paper. A sheet of paper 20×18 cm. is placed over the gel layer and pressed (rolled) just enough to ensure contact with the gel. Care is taken not to trap air under the paper (replica) and not to disturb the gel layer. The liquid phase is soaked off from the gel layer by the paper and removed after about one minute, immediately dried in an oven at a 60° temperature for 15 minutes and stained in the normal way with any of the routine staining procedures. Staining is performed by spraying the replica-paper with 0.03% diazotized sulfanilic acid in 10% Sodium Carbonate (Pauley's Reagent). Staining can also be accomplished with a saturated solution of Amido Black in Methanol-Acetic Acid (90:10 v/v is used); the staining time is 5–10 minutes. For destaining, rinse with two volumes of the 90:10 methanol and acetic acid solution mixed with one volume of $H_2O$. It is difficult to obtain low background staining without very extensive washing. The plates themselves may also be dried at about 60° C. (in an oven with air circulation) but only if the ASTROCYTIN is to be stained. For isolation purposes, the plate should only be air dried at room temperature. Overheating can lead to cracking, but this can usually be avoided with a 50°-60° temperature which dries a sephadex G-200 plate in 15-30 minutes. The dry plates are allowed to swell for 10 minutes in a mixture of methanol+$H_2O$+acetic acid (75:20:5) and stained in a saturated Amido Black in the same solvent system for five hours and subsequently washed by bathing for two hours in the same solvent before they are dried. For molecular weight determinations the distance from the starting line to the middle of each zone is measured with an accuracy of 0.05 mm. either directly on the print (replica) or on the densitogram. The result is expressed by the $R_m$ value defined as the ratio of the migration distance of the tested protein ($d_p$) to that of cytochrome C or myoglobin ($d_m$) which is used as the reference protein: Relating migration distance of tested substance to standard is the formula ($-R_m=d_p/d_m$). A straight calibration line is obtained by plotting the *logarithm* of the molecular weight of the standards used against the $R_m$. From this line the molecular weight of the unknown protein can be obtained. For most exact results six equal parts of the protein sample solution with standard, in this case, Cytochrome C, before applying to the plate. By the above TLG procedure the product ASTROCYTIN is observed as a discrete spot at a distance of approximately 0.83±0.02 with reference to the standard Cytochrome C, yielding an approximate molecular weight of 8000 for ASTROCYTIN. Several discrete products are separated in this procedure from ASTROCYTIN on the basis of slight differences in chemical structure and large differences in molecular weight. Thus, three products carried as contaminants to this point with molecular weight of approximately 64,000, 148,000 and 230,000, and one occasionally of molecular weight 32,000, have been detected and removed by the TLG methods described above. The product is ASTROCYTIN is aspirated with the gel in which it is contained, in dry form, dissolved in Solution (1) and freed of resin by centrifugation or other similar means.

The product ASTROCYTIN which has been produced at this stage is soluble in distilled water, soluble at neutral and acid pH, and insoluble at alkaline pH and has a spectrophotometric absorption peak wavelength of 280 mμ. It is a polypeptide with molecular weight, as stated above, of approximately 8000. Its covalently linked amino acids are shown by hydrolysis with 6N HCl then quantitative automatic determination to have the following average composition of amino acids:

|  | Approximate Number of Residue |
| --- | --- |
| Aspartic acid | 9 |
| Threonine | 5 |
| Serine | 6 |
| Glutamic acid | 13 |
| Proline | 4 |
| Glycine | 6 |
| Alanine | 9 |

-continued

|  | Approximate Number of Residue |
|---|---|
| Valine | 4 |
| ½ Cystine | 2 |
| Methionine | 1 |
| Isoleucine | 2 |
| Leucine | 8 |
| Tyrosine | 2 |
| Phenylalanine | 3 |
| Lysine | 8 |
| Histidine | 2 |
| Arginine | 4 |
| Approximate Total | 88 |

Cysteic acid, hydroxyproline, norleucine, ammonia, isodesmosine, desmosine, hydroxylysine, lysinonorleucine and gamma-aminobutyric acid are all absent in detectable amounts, but a trace of glucosamine may be present.

From 11 grams of the starting brain tumor tissue in EXAMPLE 1, approximately 3 mg. of purified ASTROCYTIN is produced by the above methods.

EXAMPLE 3

Production of MALIGNIN-Precursor in Artificial Cancer Cell Culture

Generally, sterile technique is scrupulously maintained.

All solutions (e.g. Hank's Balanced Salt (BSS), F-10 Nutrient medium, fetal calf serum trypsin solution) are incubated at about 35° C. in a water bath for approximately 20 minutes or more before use.

Cells are removed from tumor tissue and grown in vitro for many generations using a suitable medium, such as described below. Pre-rinse beakers to be used with a sterilizing solution, for example, 12-proponal plus Amphyl or creoline solution.

In the preferred embodiment, the artificial cancer cells (i.e., cells grown in vitro for many generations) are grown in 250 ml. flasks. The liquid medium in which the cells are growing is discharged into the pre-rinsed beakers. The cells are then washed gently with 5–10 ml. of Hank's BSS or other similar solution for about 30 seconds. Avoid agitation. All walls and surfaces are washed. The solution is clarified of cells by centrifugation in the cold from 10 minutes at 3,000 rpm. The medium is poured into a beaker as above. Add a small amount of buffered proteinase enzyme solution and rinse quickly to avoid digestion of the cells. In the preferred method, 1–2 ml. of trypsin solution (EDTA) is added and rinsed for only 10 seconds. Pour off the trypsin solution.

Add a similar volume of fresh trypsin solution and incubate until the cells are seen to be separated from the walls of the chamber through microscopic observation. This usually requires 5–10 minutes. Add a suitable growth medium, such as 50 ml. of a solution of 7–10 percent solution of fetal calf serum in 100 ml. of F-10 Nutrient medium.

Twenty-five ml. of the fresh medium with cells is tranferred to a new growth chamber for propagation and the remaining 25 ml. is kept in the first chamber for propagation. Both chambers are placed in an incubator at 35° C. for approximately seven days. By the procedure of this Example to this point, an artificial cancer cell culture is divided into two fresh cultures approximately every seven days. This entire procedure may be repeated as often as desired, at approximately seven-day intervals, for each growth chamber. Thus, the number of cells growing in vitro may be doubled approximately every seven days.

The cells may be extracted for the production of MALIGNIN after approximately seven days of growth. For example, cells growing in each 250 ml. growth chamber as described above, may be recovered as follows.

The medium is transferred to a centrifuge tube and centrifuged at 3,000 rpm in the cold for 10 minutes. The medium is discarded. The cells remaining in the growth chamber are scraped from the chamber walls and washed into the centrifuge tubes with neutral buffer solution. The cells are washed twice with neutral buffer solution, centrifuged again at 3,000 rpm in the cold, and the medum is discarded. The washed cells are suspended in 10 ml. of neutral phosphate buffer until ready for extraction of crude MALIGNIN-Precursor-Containing fraction.

EXAMPLE 4

Production of Crude MALIGNIN-Precursor-Containing Fraction

Washed cells suspended in neutral buffer from EXAMPLE 3 are mechanically disrupted under conditions which avoid denaturation of most proteins. In the preferred method, the washed cells are treated in the cold with a sonifier for 20 seconds.

After sonification the cell residues are centrifuged at 30,000 rpm for 30 minutes and the supernatant decanted. Ten ml. aliquots of buffer solution are used to wash remaining cells from the chamber and these are added to the remaining cell residues. Sonify and centrifuge as above and combine the supernatants. Repeat the process once more.

The combined supernatant is perevaporated to reduce the approximate 30. ml. volume to about 6–7 ml. An aliquot is taken for total protein analysis and the remainder is fractionated according to the methods of EXAMPLE 1 for ASTROCYTIN Precursor.

EXAMPLE 5

Production of Purified MALIGNIN Product from Crude MALIGNIN-containing Fraction

The product MALIGNIN is further isolated from contaminants by the methods of EXAMPLE 2 for ASTROCYTIN.

In the TLG step of the preferred embodiment, the product MALIGNIN is observed as a discrete spot at a distance of approximately 0.91±0.02 with reference to the standard cytochrome C, yielding an approximate molecular weight of 10,000 for MALIGNIN.

The product MALIGNIN which has been produced at this stage is soluble in distilled water, soluble at neutral or acid pH, and insoluble at alkaline pH and having a spectrophotometric absorption peak of 280 m$\mu$. It is a polypeptide with molecular weight of approximately 10,000. Its covalently linked amino acids are shown by hydrolysis with 6N HCl then quantitative determination to have the following average composition of amino acids:

|  | Approximate Number of Residues |
|---|---|
| Aspartic Acid | 9 |
| Threonine | 5 |

-continued

| | Approximate Number of Residues |
|---|---|
| Serine | 5 |
| Glutamic Acid | 13 |
| Proline | 4 |
| Glycine | 6 |
| Alanine | 7 |
| Valine | 6 |
| ½ Cystine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| Approximate Total | 89 | the amino acids cysteic acid, hydroxyproline, norleucine, ammonia, isodesmosine, desmosine, hydroxylysine, lysinonorleucine and gamma-aminobutyric acid being absent in detectable amounts.

A typical yield of pure MALIGNIN from twelve 250 ml. reaction chambers of EXAMPLE 3 together is approximately 1 ml. of MALIGNIN.

EXAMPLE 6

Hydrolytic Cleavage of RECOGNINS

A solution of RECOGNIN, in this case either Astrocytin or Malignin at pH between 1 and 2 is allowed to stand in the cold. After 7 to 14 days, TLG chromatography shows the product to have been reduced in molecular weight by approximately 200. When the solution is allowed to stand longer, further units of approximately 200 molecular weight are cleaved every 7 to 10 days. Thus with Astrocytin the molecular weight is reduced from 8,000, and with MALIGNIN the molecular weight is reduced from 10,000, in each case by units of approximately 200 sequentially.

The physicochemical specificities of ASTROCYTIN are retained by each product down to approximately 4,000 molecular weight. The physicochemical specificities of Malignin are retained by each product down to approximately 5,000 molecular weight. This is shown by Ouchterlony gel diffusion tests against Anti-Astrocytin and Anti-Malgnin, respectively.

This cleavage can also be accomplished enzymatically, as with trypsin and other proteinases, with similar results.

The molecular weights of these compounds prepared by hydrolytic cleavage of RECOGNINS may be approximately defined by the following formulae:

For products having the physicochemical specificities of Astrocytin; $4000+200x=Y$ For products having the physicochemical specificities of Malignin; $5000+200x=Y$ wherein Y is the molecular weight of the product and X is an integer from 0 to 19.

EXAMPLE 7

Production of Artificial Tissue or Organ with RECOGNINS

A rigid walled tube of plastic, metal, or other suitable rigid material is dipped in or impregnated with a highly concentrated (i.e., 10 mg./ml.) viscous solution of RECOGNIN, in this case either Astrocytin or Malignin, until all surfaces are fully coated with the RECOGNIN. Alternately, RECOGNIN solution is passed through and around the tube under pressure until all surfaces are fully coated. The tube is then dried in air or in vacuo, or lyophilized. The process of coating is repeated several times in order to build up multiple molecular layers of RECOGNIN coating.

The tube is now ready to be placed in a cavity or in a tissue which contains Astrocytin or Malignin-like precursors in the neighboring tissue or fluid of a living mammal. This artificial tissue or organ may be used to minimize or eliminate reaction which foreign substances without RECOGNIN coating would incite.

Artificial tissues or organs of other geometries may similarly be produced.

EXAMPLE 8

Production of TARGET reagents from RECOGNINS

ASTROCYTIN, prepared as in EXAMPLE 2 above, or MALIGNIN, prepared as in EXAMPLES 5 above, is complexed with a carrier to produce TARGET reagent.

In the preferred embodiment, ASTROCYTIN or MALIGNIN is dissolved in 0.15 M. $NaH_2PO_4$—citrate buffer, pH 4.0. A bromoacetyl-resin, for example bromoacetylcellulose (BAC) having 1.0 to 1.5 milliequivalents Br per gram of cellulose, stored in the cold, is prepared in 0.15 M $NaH_2PO_4$ buffer, pH 7.2. Convert the buffer to pH 4 by pouring off the pH 7.2 buffer solution and adding 0.15 M $NaH_2PO_4$—citrate buffer, pH 4.0. The ASTROCYTIN OR MALIGNIN solution and the BAC solution are stirred together (10:1 BAC to RECOGNIN ratio) for 30 hours at room temperature, then centrifuged.

It is preferred that all sites on the BAC which are available to bind to RECOGNIN be bound. This may be accomplished as follows. The supernatant from the immediately preceding step is lyophilized and the protein content determined to indicate the amount of ASTROCYTIN or MALIGNIN not yet complexed to BAC. The complexed BAC-ASTROCYTIN (or BAC-MALIGNIN) is resuspended in 0.1 M bicarbonate buffer pH 8.9, stirred 24 hours at 4° to permit the formation of chemical bonds between the BAC and the ASTROCYTIN or MALIGNIN. After the 24 hours, the suspension is centrifuged and supernatant analyzed for protein. The complexed BAC-ASTROCYTIN or BAC-MALIGNIN is now resuspended in 0.05 M aminoethanol—0.1 M bicarbonate buffer pH 8.9 in order to block any unreacted bromine. The suspension is centrifuged, and the supernatant is kept but not analyzed because of the presence of aminoethanol. Removal of all unbound ASTROCYTIN or MALIGNIN in then accomplished by centrifugation and resuspension for three washings in 0.15 M NaCl until no absorbance is measured on the spectrophotometer at 266 mμ. The BAC-ASTROCYTIN or BAC-MALIGNIN complex is now stirred in 8 M urea for 2 hours at 38° C., centrifuged, then washed (three times usually suffices) with 8 M urea until no absorbance is shown in the washings at 266 mμ. The complex is then washed with 0.15 M NaCl two times to rid of urea. The complex is then stirred at 37° C. in 0.25 M acetic acid for 2 hours to demonstrate its stability. Centrifuge and read supernatant at 266 mμ—no absorbance should be present. This chemically complexed BAC-ASTROCYTIN or BAC-MALIGNIN is therefore stable and can now be used as a reagent in the methods described below; in this stable reagent form it is referred to as TARGET (TOPO-GRAPHIC-ANTIGEN-LIKE-REAGENT-TEMPLATE) because it is a synthetically produced complex whose physical and chemical properties mimic the stable cell-bound precursor of ASTROCYTIN or MALIGNIN when it is in a potential reactive state with serum components. For storing, TARGET reagent is centrifuged and washed until neutralized with 0.15 M NaH$_2$PO$_4$ buffer pH 7.2.

TARGET reagents may be prepared from bromoacetyl liganded carriers other than cellulose, such as bromoacetylated resins or even filter paper.

EXAMPLE 9

Production of antisera to Astrocytin, Malignin and TARGET

Antisera to Astrocytin, Malignin or TARGET reagents may be produced by inducing an antibody response in a mammel to them. The following procedure has been found to be satisfactory.

One mg. of RECOGNIN (Astrocytin or Malignin) is injected into the toe pads of white male rabbits with standard Freund's adjuvant, and then the same injection is made intraperitoneally one week later, again intraperitoneally ten days and, if necessary, three weeks later. Specific antibodies may be detected in the blood serum of these rabbits as early as one week to ten days after the first injection. The same procedure is followed for TARGET antigen by injecting that amount of TARGET which contains 1 mg. of Astrocytin or Malignin as determined by Folin-Lowry determination of protein.

The specific antibody to Astrocytin is named Anti-Astrocytin. The specific antibody to Malignin is named Anti-Malignin. Similarly, the specific antibody to TARGET reagent is named Anti-Target.

These antibodies show clearly on standard Ouchterlony gel diffusion tests for antigen-antibody reactions with specific single sharp reaction lines produced with their specific antigen.

The pressure of specific antibodies in serum can also be tested by the standard quantitative precipitin test for antigen-antibody reactions. Good quantitative precipitin curves are obtained and the micrograms of specific antibody can be calculated therefrom.

Further evidence of the presence of specific antibodies in serum can be obtained by absorption of the specific antibody Anti-Astrocytin onto Bromoacetyl-cellulose-Astrocytin (BAC-Astrocytin) prepared above. The antiserum containing specific Anti-Astrocytin can be reacted with BAC-Astrocytin. When the serum is passed over BAC-Astrocytin only the specific antibodies to Astrocytin bind to their specific antigen Astrocytin. Since Astocytin is covalently bound to Bromoacetyl-cellulose the specific antibody, Anti-Astrocytin, is now bound to BAC-Astrocytin to produce BAC-Astrocytin-Anti-Astrocytin Anti-Astrocytin (BACA-Anti-Astrocytin). This is proved by testing the remainder of the serum which is washed free from BAC-Astrocytin. On standard Ouchterlony diffusion no antibodies now remain in the serum which will react with Astrocytin. It is therefore concluded that all specific antibodies (Anti-Astrocytin) previously shown to be present in the serum, have been absorbed to BAC-Astrocytin. Furthermore, when Anti-Astrocytin is released from its binding to BAC-Astrocytin it is thereby isolated free of all contaminating antibodies. This release of Anti-Astrocytin may be accomplished by washing the BACA-Anti-Astrocytin compled with 0.25 M acetic acid (4° C., 2 hrs.) which has been shown above not to break the BAC-Astrocytin bond.

Still further evidence of the presence of specific antibodies in serum can be obtained by adsorption of the specific antibody Anti-Malignin onto Bromoacetyl-cellulose-Malignin (BAC-Malignin) prepared above. The antiserum containing specific Anti-Malignin can be reacted with BAC-Malignin. When the serum is passed over BAC-Malignin only the specific antibodies to Malignin bind to their specific antigen Malignin. Since Malignin is covalently bound to Bromoacetyl-cellulose the specific antibody, Anti-Malignin, is now bound to BAC-Malignin-Anti-Maligin (BACM-Anti-Malignin). This is proved by testing the remainder of the serum which is washed free from BAC-Malignin. On standard Ouchterlony diffusion no antibodies now remain in the serum which will react with Malignin. It is therefore concluded that all specific antibodies (Anti-Malignin) previously shown to be present in the serum, have been adsorbed to BAC-Malignin. Furthermore, when Anti-Malignin is released from its binding to BAC-Malignin it is thereby isolated free of all contaminating antibodies. This release of Anti-Malignin may be accomplished by washing the BACM-Anti-Malignin complex with 0.25 M acetic acid (4° C., 2 hrs.) which has been shown above not to break the BAC-Malignin bond.

The antibodies to TARGET show clearly on standard Ouchterlony gel diffusion tests for antigen-antibody reactions with specific single reaction lines produced with TARGET which show a line of identity with the line of reaction to ANTI-ASTROCYTIN or ANTI-MALIGNIN antisera (i.e., that produced to the injection of ASTROCYTIN or MALIGNIN themselves). Some rabbits, it has been noted, have levels of ANTI-TARGET in their blood prior to being injected with TARGET. These ANTI-TARGET substance, when reacted specifically with TARGET reagent as to be described in tests of human sera, lead to the production of approximately equivalent amounts of the two types of TAG, S-TAG and F-TAG (see later EXAMPLES).

EXAMPLE 10

Detection of Malignant Tumors by Quantitative Production in vitro of TARGET-ATTACHING-GLOBULINS (TAG) from Biological Fluids TARGET reagent prepared in accordance with EXAMPLE 8 is washed to remove any unbound RECOGNIN which may be present due to deterioration. The following procedure is satisfactory. TARGET reagent is stirred for two hours at 37° C. with acetic acid, centrifuged, the supernatant decanted, and the optical density of the supernatant read at 266 m$\mu$. If there is any absorbance, this wash is repeated until to further material is solubilized. The TARGET is then resuspended in phosphate buffered saline, pH 7.2. (Standard S-TAG and F-TAG purified from previous reactions of human serum by the procedure described below can be used if available, as reference standards to test the TARGET reagent, as can whole rabbit serum which has been determined to contain S-TAG and F-TAG by other TARGET preparations).

The Slow-Binding (S-TAG) determination is performed as follows: Frozen serum stored more than a few days should not be used. Serum is carefully prepared from freshly obtained whole blood or other body fluid by standard procedures in the art. The following procedure has been found to be satisfactory. Blood is allowed to clot by standing for 2 hours at room temperature in a glass test tube. The clots are separated from the walls with a glass stirring rod, and the blood allowed to stand at 4° C. for a minimum of 2 hours (or overnight). The clots are separated from the serum by centrifuging at 20,000 rpm at 4° C. for 45 minutes. The serum is decanted into a centrifuge tube and centrifuged again at 2000 rpm at 4° C. for 45 minutes. The serum is decanted and a 1% Solution of Methiolate (1 g. in 95 ml. water and 5 ml. 0.2 M bicarbonate buffer pH 10) is added to the extent of 1% of the volume of serum.

Serum samples, prepared by the above or other procedures, of 0.2 ml each are added to each of 0.20 ml. aliquots of TARGET suspension reagent containing 100–200 micrograms of RECOGNIN per 0.20 ml. TARGET reagent, in duplicate determination. The suspension is mixed at 4° C. in a manner to avoid pellet formation. For example, small rubber cap rapid shaken may be used for 1–2 seconds and then, with the tubes slightly slanted, they may be shaken in a Thomas shaker for about 2 hours or more. The TARGET reagent and protein bound to it are separated from the serum. One of the procedures which has been found to be satisfactory is the following. The tubes are then centrifuged at 2000 rpm for 20 minutes at 4° C., the supernatant decanted, the pellet which is formed by centrifugation washed 3 times by remixing and shaking at room temperature with 0.2–0.3 ml of 0.15 M Saline, centrifuged and the supernatants discarded.

The protein which remains attached to the TARGET is cleaved therefrom and quantitatively determined. For example, 0.2 ml. of 0.25 M acetic acid is added, the suspension shaken for 1 to 2 seconds with a rubber cap shaker, then in a Thomas shaker for about 2 hours in a 37° C. incubator. The tubes are centrifuged at 2000 rpm at 4° C. for 30 minutes. The supernatant is carefully decanted to avoid transfering particles and the optical density of the supernatant is read at 280 m$\mu$. The value of the optical density is divided by a factor of 1.46 for results in micrograms per ml. serum protein (S-TAG). Duplicate determinations should not vary more than 5%. Any other procedure effective for determining protein content may be used, such as Folin-Lowry determination, but standards must be specified to determine the range of control and tumor values of S-TAG and F-TAG concentration.

The Fast-Binding (F-TAG) determination is performed as follows: Frozen serum stored more than a few days should not be used. Serum is carefully prepared from freshly obtained whole blood or other body fluid by standard procedures in the art. The procedure given above in this EXAMPLE for serum preparation is satisfactory.

Serum samples, prepared by the above or other procedures are allowed to stand at 4° C. for 10 minutes less than the total time the S-TAG serum determinations were allowed to be in contact with TARGET reagent above (e.g., 1 hour 50 minutes if a "two hour" S-TAG determination was made). This procedure equilibrates the temperature histories of S-TAG and F-TAG determinations.

Add 0.2 ml. samples of the temperature equilibrated serum to each of 0.20 ml. aliquots of TARGET suspension reagent contains 100–200 micrograms of RECOGNIN per 0.20 ml. TARGET reagent, in duplicate determination. The suspension is then mixed at 4° C. for approximately 10 minutes in a manner to avoid pellet formation. For example, a small rubber cap rapid shaker may be used for 1–2 seconds and then, with the tubes slightly slanted, they may be shaken in a Thomas shaker for approximately 10 minutes. The TARGET reagent and protein bound to it are separated from the serum. One of the procedures which has been found to be satisfactory is the following. The tubes are then centrifuged at 2000 rpm for 20 minutes at 4° C., the supernatant decanted, the pellet which is formed by centrifugation washed 3 times by remixing and shaking at room temperature with 0.2–0.3 ml. of 0.15 M Saline, centrifuged and the supernatants discarded.

The protein which remains attached to the TARGET is cleaved therefrom and quantitatively determined. The procedure described above in this EXAMPLE for determining S-TAG concentration is satisfactory. Any other procedure effective for determining protein content may be used, such as Folin-Lowry determination, but standards must be specified to determine the range of control and tumor values of S-TAG minus F-TAG concentration.

The final results are expressed as TAG micrograms per ml. of Serum, and equal S-TAG minus F-TAG. TAG values in non-brain-tumor patients and other controls currently range from zero (or a negative number) to 140 micrograms per ml. serum. TAG values in the first patients studied, brain tumor patients, ranged from 141 to 500 micrograms per ml. of serum. In the first "blind" study of 50 blood samples conducted according to the procedures of this EXAMPLE utilizing TARGET reagent prepared from Astrocytin and bromoacetylcellulose, 11 of 11 brain tumors and 28 of 32 normals were correctly identified. One of the 4 supposed normals (i.e., non-brain tumor controls) turned out to have a cancer of the thyroid gland which had apparently been successfully treated some years before. The three remaining normals were individuals aged 60–70 who were in poor health, possibly having nondiagnosed cancer. Of the remaining 7 samples, three out of three cases of Hodgkin's Disease were correctly identified; one sample in the tumor range (141–500 $\mu$g. TAG/ml.) corresponded to patients having respectively, an intracranial mass diagnosis uncertain but non-tumor, and osteosarcoma (non-brain tumor) and a melanotic sarcoma (non-brain tumor).

Subsequent blind studies conducted according to the procedures of this example utilizing TARGET reagent prepared from MALIGNIN and bromoacetylcellulose correctly identified three out of three malignant brain tumors and all normals, then were continued as detailed in EXAMPLE 10A which follows.

EXAMPLE 10A

Determination of Anti-Malignin Antibody in 1,026 Cancer Patients and Controls: A Seven-Year Nine Hospital Blind Study The antibody to malignin, a cancer cell 10,000 Dalton polypeptide of known composition, was quantitatively determined blind by specific immuno-adsorption in 1,094 serum specimens from 1,026 cancer patients and controls. Anti-malignin antibody, known to be cytotoxic to cancer cells in vitro, was elevated in 92.7% of sera from patients with clinically and pathologically active cancer (mean 273.7±156.5 micrograms/ml) compared with healthy normal subjects (mean 59.1±27.0 micrograms/ml) in a broad range of types of malignancy in support of the hypothesis that malignin is a general transformation antigen. The antibody was in the normal range (0-134 micrograms/ml) in 100% of sera of healthy normal subjects (first control group), in 94.6% of sera of out-patient hospital non-cancer controls (mean 64.3±46.3 micrograms/ml) (second control group) and in 91.2% of sera of in-patient medical-surgical disorder non-cancer patients (mean 81.2±67.3 micrograms/ml) (third control group). That only an active cancer state appears to be associated with elevated antibody levels is supported by the finding that the antibody was in the normal range in 94.2% of sera from cancer patients who had been successfully treated and clinico-pathologically showed 'no evidence of disease' at the time of the determination (fourth control group) (mean 70.1±36.7 micrograms/ml). None of the four control groups was statistically significantly different from each other, but each control group differed from the active cancer group at a level of $P<0.000001$. Of the 109 cancer patients who had antibody levels below 135 micrograms/ml, 90 (83.3%) were dead within one year (mean 4.4±3.5 months). Of the 76 active cancer patients who could be followed and who were still alive beyond one year and up to 46 months (mean 22.0±8 months) after the antibody determination, 68 (89.5%) had had antibody levels above 135 micrograms/ml. The relationship of the concentration of anti-malignin antibody to survival suggested by these data as well as some diagnostic and therapeutic implications are noted.

A general transformation antigen is one which is common to the process of malignant transformation rather than to the particular cell type involved. The general antigen therefore differs from cell-specific tumor markers which are related to the products of the particular type of cell transformed, as in the case of insulin or thyroid hormone excesses produced by pancreatic or thyroid neoplasms respectively (7). Malignin, a 10,000 dalton polypeptide from malignant glial cells, with a high content of glutamic acid and espartic acid and a high ratio of these two amino acids to histidine, reported in 1975 (1-3), and its close structural relatives astrocytin, recognin L (lymphoma) and recognin M (mammary carcinoma) (2,4) are members of what appears to be the first chemically and immunologically defined family of general transformation antigens. These antigens, or anti-malignin antibody which reacts with each, have been determined in the cells and sera of patients with a variety of neoplasms, in induced malignant transformations in animals and in the cells and supernates of malignant cells growing in tissue culture (5-7,12). Other transformation antigens, not quite as general but broad in representation, are now being identified in other laboratories in experimental cell transformations induced by chemical and viral means (8,9).

Over the past seven years we have examined the possible relation of malignin and anti-malignin antibody to human cancer states. Previous tumor-associated antigens studied in humans, such as the carcinoembryonic antigens (10) have exhibited varying demonstrability in different types of cancer and low concordance with clinical diagnoses. Perhaps due to the fact that none have had constant chemically defined composition or mode of production, the inconstantly released mixtures of antigens rather than a potentially more constant level of specific antibody have had to be measured in serum. Malignin is produced in constant tissue culture of malignant cells, is of known and reproducible composition, and its antibody has been demonstrated to be present in and isolated from the serum of patients with cancer (6,7). The antibody and antigen studies reported here support the apparently ubiquitous distribution of the malignin antigen or its very close structural relatives in active cancer of all types examined.

METHODS

Patients and Controls (a) Serum Anti-Malignin Antibody Studies

Cancer patients were chosen by the clinical investigators at each of nine hospitals from various types of cancer in the approximate frequency of their rate of occurrence in their population or of the investigator's particular interest (see Table 1). Untreated as well as treated cases were accepted. Of the resultant 500 cancer sera studied, 247 (49.4%) were from patients who had clinically and pathologically defined and successfully treated cancer up to 15 years earlier and had no clinical or pathological evidence of disease at the time the antibody was determined (fourth contol group, below). Of the active cancer group, 76 patients could be followed who were still alive beyond one year and up to 46 months. Four control groups were studied: (1) 59 healthy normals (60 sera); (2) 56 hospital out-patients with some symptoms but without definite clinical diagnosis (56 sera); (3) 258 hospital in-patients with definite medical-surgical diagnoses (261 sera); and (4) the 86 cancer patients referred to above who had no evidence of disease at the time of the determination. The medical-surgical diagnoses in the third control group included bacterial infections (26 sera), viral infections (28 sera), trauma (8 sera), cardiovascular disorders (30 sera), gastrointestinal and hematopoietic disorders (39 sera), thoracic disorders (6 sera), obstetrical and gynecological disorders (7 sera), genitourinary disorders (11 sera), endocrine metabolic and arthritic disorders (22 sera), neurologic disorders (62 sera), psychiatric disorders (6 sera), and skin disorders (16 sera). In addition to the above randomly collected sera, selective blind studies have been initiated by not completed on several specific groups: 45 patients with multiple sclerosis (49 sera) and 57 with benign tumors (74 sera), as well as on 31 blood relative ('relatives') of cancer patients (31 sera), on people in contact with cancer patients, that is, 54 non-blood relatives and hospital staff ('contacts') (63 sera). 84% of the sera came from the Medical College of Ohio at Toledo.

(b) Immunochemical Methods

Serum anti-malignin antibody was quantitatively determined by an immunoabsorption method previously described in which the serum antibody is specifically adsorbed to immobilized malignin ('Target' reagent) in a 2-hour (slow) and a 10-minute (fast) reaction, then released in soluble form and read by optical density at 280 millimicrons as micrograms of antibody protein (11). The values of anti-malignin antibody are expressed as net Target-attaching-globulins ('Net TAG') calculated: 2-Hour immunoadsorption Slow (S) TAG less the 10-Minute immunoadsorption Fast (F) TAG. All values given represent Net TAG unless otherwise noted. The Net TAG does not appropriately reflect the antibody elevation when the F-TAG is markedly elevated to between 270 and 1100 micrograms/ml. In these instances, seen rarely in the four control groups (2 of 464 sera, 0.4%), but in 58 of 247 active cancer sera (23.5%), the S-TAG values are also elevated to above 400 and as much as 12,00 micrograms/ml. In the accompanying figures, to distinguish these cases of extraordinary increase in both forms of antibody, rather than adding the values for the two forms, only the S-TAG has been plotted as open circles. These cases have been examined statistically in two ways, separately, and as part of the clinically determined active cancer group. The antibody determinations were performed blind on the coded speciments of sera by laboratory personnel who were in a different center than the one in which the specimens were collected.

(c) Correlation of Clinical and Laboratory Data

Correlations were made for each patient after completion and recording of both clinical and laboratory data separately. The error for these correlations in terminal cases is likely to be very small since it involved pathologically confirmed cancer and two reliable dates: the date of the antibody determination and the date of death. For each of 206 of the 247 active cancer cases, in addition to the absence of their names from the tumor registry of deaths, it was possible to verify by contacting each patient or their physician that the patient was still alive at the end of one year. For 41 of these cases, the contact verification either was not possible or possible only to the tenth month. Since most of these 41 cases were from the first two years of the study, when clinically terminal patients were actively excluded from the study, this is not likely to represent an appreciable error. At most, the number in the active cancer group would be reduced and the number in the terminal group increased, each by 41, neither of which would significantly influence the conclusions reached except for the value of the mean for the antibody in the terminal group which would be increased. In the statistical comparison of the groups, values of P 0.01 were considered statistically significant. The only comparison of those found not significant under these criteria which approached but did not quite reach the 0.05 level was between the first two contol groups FIG. 1).

RESULTS

FIG. 1 shows the concentration of anti-malignin antibody, in micrograms/ml serum in individual sera, in the four control groups and the active cancer group: that is, (1) healthy normals, (2) cancer patients showing no evidence of disease after successful treatment, (3) outpatients (non-cancer) with medical-surgical symptoms but without defined disorders, (4) in-patients (non-cancer) with defined medical-surgical disorders, and (5) patients with active cancer who lived one year or longer. While the four control groups did not differ from each other at a statistically significant level, each differed from the active cancer group at the significant level of P 0.000001.

FIG. 2A shows the concentration of anti-malignin antibody in individual sera of patients with terminal cancer, that is, those who died within one year (mean 4.4±3.5 months). The concentration of antibody in this group differs statistically from the active cancer group at a level of P<0.000001. Together with the data shown in FIG. 1, it may be seen that 90 of 108 cancer patients (83.3%) who had antibody levels below 135 micrograms/ml died within one year. In contrast, of the 76 active cancer patients who were longer term survivors and who could be followed 13 to 46 months (mean 22.3±8) after the antibody determination, 68 (89.5%) had had elevated antibody levels. FIG. 2B shows seven examples of the decrease before death observed in individual patient's serum anti-malignin antibody levels when determined serially.

Table 1 shows the types of cancer patient studied, and the distribution of samples between active disease, terminal disease and no evidence of disease in each type of cancer. The distribution of type of cancer is fairly typical with the exception of an excess number of brain cancer cases which was the initial focus of interest of the study.

In the beginning blind study in each of the non-random preselected groups the antibody level was elevated in the sera of 20.4% of patients with multiple sclerosis, 31.1% of patients with benign tumors, 30.2% of 'contacts' of active cancer patients, and 38.7% of blood relatives of active cancer patients.

EXAMPLE 10A

TABLE I

DISTRIBUTION OF NUMBER OF SERUM ANTI-MALIGNIN ANTIBODY DETERMINATION ACCORDING TO TYPE OF MALIGNANCY AND CLINICAL STATUS

| TYPE OF MALIGNANCY | TOTAL NUMBER | CLINICAL STATUS | | |
|---|---|---|---|---|
| | | Active Disease | No Evidence Disease | Terminal |
| Carcinoma of: | | | | |
| Lung | 38 | 11 | 1 | 26 |
| Larynx | 3 | 2 | | 1 |
| Breast | 67 | 26 | 27 | 14 |
| Uterus | 5 | 1 | 1 | 3 |
| Cervix | 6 | 3 | | 3 |
| Ovary | 11 | 3 | 3 | 5 |
| Vulva | 1 | | | 1 |
| Colon | 37 | 18 | 3 | 16 |
| Rectum | 13 | 9 | 2 | 2 |
| Stomach | 2 | 1 | | 1 |
| Oesophagus | 3 | 1 | | 2 |
| Bile Duct | 1 | | | 1 |
| Prostate | 13 | 7 | 4 | 2 |
| Bladder | 12 | 5 | 4 | 3 |
| Urethra | 1 | 1 | | |
| Kidney | 15 | 6 | 5 | 4 |
| Testis | 7 | 1 | 5 | 1 |
| Thyroid | 4 | 4 | | |
| Pancreas | 4 | | | 4 |
| Adrenal | 1 | | | 1 |
| Skin | 5 | 1 | 3 | 1 |
| Undifferentiated | 14 | 9 | | 5 |
| Hodgkins' Disease | 14 | 8 | 3 | 3 |
| Lymphoma | 25 | 15 | 9 | 1 |
| Multiple Myeloma | 15 | 10 | 2 | 3 |
| Acute Myelogenous Leukemia | 3 | 2 | | 1 |
| Acute Lymphocytic Leukemia | 1 | | 1 | |
| Chronic Myelogenous Leukemia | 8 | 7 | | 1 |
| Chronic Lymphocytic Leukemia | 8 | 4 | 2 | 2 |
| Fibrosarcoma | 1 | 1 | | |
| Melanotic Sarcoma | 15 | 8 | 4 | 1 |
| Osteogenic Sarcoma | 6 | 1 | 1 | 4 |
| Rhabdomyosarcoma | 4 | | 1 | 3 |
| Liposarcoma | 1 | 1 | | |
| Hemangioblastoma | 1 | 1 | | |
| Histiocytoma | 1 | | | 1 |
| Brain Cancer | 133 | 80 | 2 | 51 |
| Retinoblastoma | 1 | | 1 | |
| | 500 | 247 | 86 | 167 |

Legend for FIG. 1:

EXAMPLE 10A Concentration of anit-malignin antibody in flour control groups and in active cancer patients. Solid circles, Net TAG; open circles, S-TAG (F-TAG excess). See Methods for details.

Figure 2:
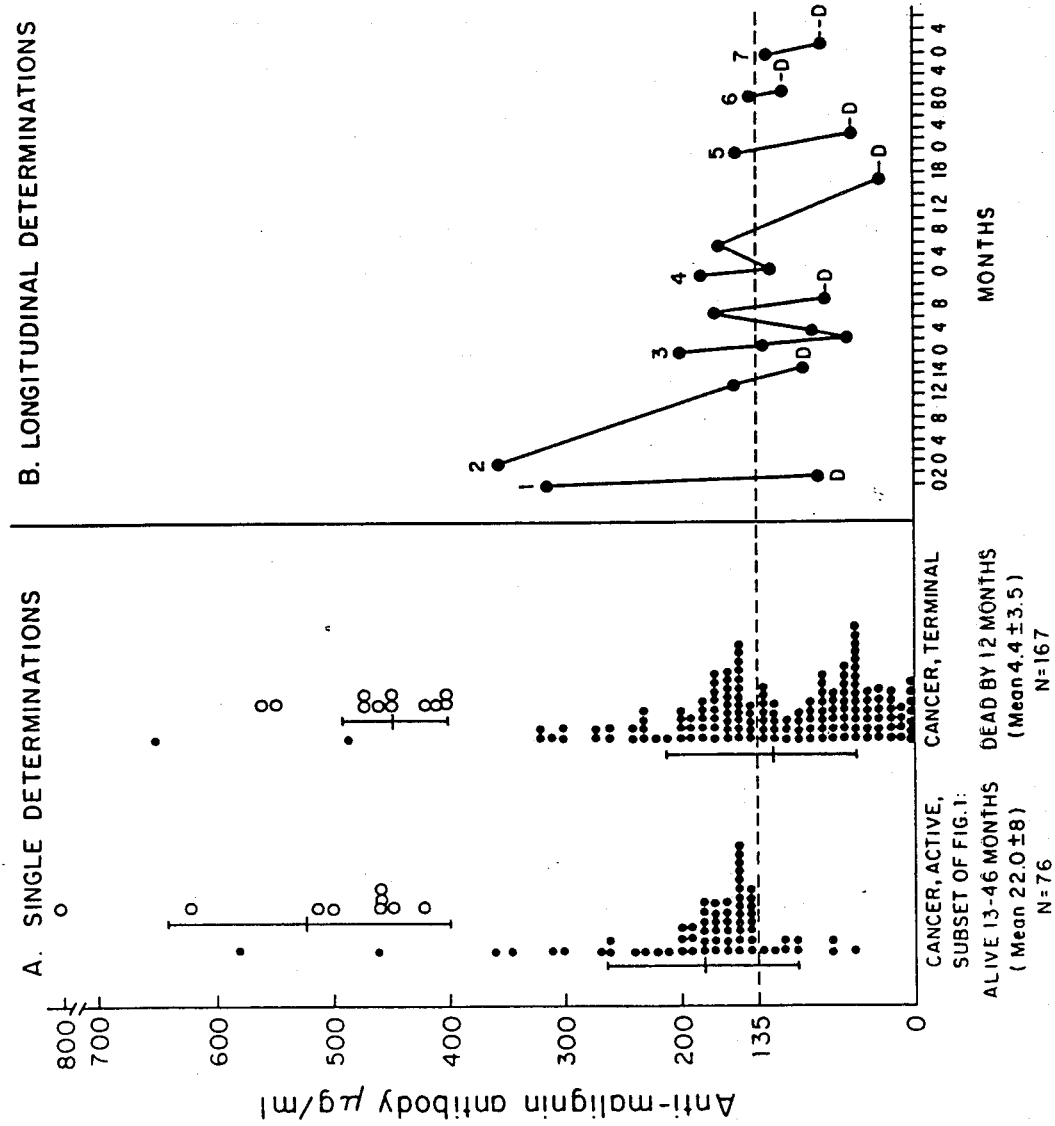

Legend for FIG. 2:
EXAMPLE 10A Relation of level of anti-malignin antibody to terminal clinical state. Solid circles, Net TAG; Open circles, S-TAG excess). See Methods for details.
A. Single blind determination in individual patients.
B. Longitudinal blind determinations on seven individual cancer patients (1 through 7) whose death (D) occurred 1 to 4 months from date last specimen determined.

DISCUSSION

The data obtained in this blind study are consistent with the previous evidence that malignin is a general transformation antigen. Thus rather than being restricted to particular cell types, anti-malignin antibody was elevated significantly above normal levels, and malignin was visualized in cells, in patients with a broad variety of active cancer (Table 1 and Methods b.) That the antibody was in the normal range in 94.2% of patients who had been successfully treated and at the time of the antibody determination showed no evidence of disease, suggests that an active cancer state is required to maintain elevated antibody levels. In the separation of healthy normal subjects from active cancer patients by determination of anti-malignin antibody, all healthy normals had values below 135 (mean $59.1 \pm 27.0$) micrograms/ml and there were no 'false positives', while in the active cancer group, 92.7% showed elevated values of antibody (mean $273.7 \pm 156.5$ micrograms/ml). The healthy normal and the active cancer groups differed at a level of $P < 0.000001$ for the whole active cancer group, as well as for each of the two subgroups shown in FIG. 1.

As medically-ill subjects are brought into the comparison (FIG. 1) the mean levels of concentration of antibody are seen to shift slightly but no significantly upward. In the out-patient non-cancer group, 94.6% were still in the normal range, and 5.4% were in the elevated range. In the in-patient, more clearly ill, positively diagnosed (but apparently non-cancer) medical-surgical group, 91.2% were still in the normal range, and 8.8% were in the elevated range. These two control groups were not statistically significantly different from the healthy normal control group but each differed from the active cancer group at a level of $P < 0.000001$. It might be expected that compared with healthy normals, the incidence of cancer would be greater in medically ill patients and that some of these cancer cases might not yet be clinically diagnosable. How many of these presumptive 'false positives' actually represent occult cancer not yet clinically detected cannot be predicted, but it is relevant to note that six additional 'false positives' were found from one to 19 months later actually to have clinically and pathologically proven cancer.

The data in the preselected groups, although blind, were not randomly collected as were those in FIGS. 1 and 2 and therefore cannot be pooled with them. Each of these preselected groups is considered too small to form conclusions because of heterogeneity of each and the complexity of the implications raised by the data, but they are included as preliminary data for the sake of completeness. There is a possibility that in the destructive and immune reactions in the nervous system in multiple sclerosis that a higher false positive rate may occur. Some of this may represent misdiagnosed central nervous system malignancy. Sera from patients with benign tumors might be expected to show a higher false positive rate consistent with the borderline area in clinico-pathological diagnosis between benign and malignant growths. Anti-malignin antibody levels and the demonstration of malignin in cells may in the future help to clarify the definition in this group. The observation of a higher incidence of elevated anti-malignin antibody in contacts of active cancer patients (compared with healthy normals $P < 0.001$) is in agreement with several previously published studies on other tumor indexes demonstrating the same curiouss phenomenon (14 clinical studies and one laboratory study cited in reference 14). Whether this represents some form of immunization against a transmittable agent, either the malignin antigen itself or a substance which induces transformation and thus the appearance of the antigen, needs more work to clarify. Finally, the greatest incidence of antibody elevation in a 'non-cancer' group is observed in the blood relatives of active cancer patients. Whether this representss a response to actual cell transformation, a genetically determined high level of production of the antibody for immunosurveillance, or the same phenomenon as that observed in the 'contacts' group is unknown. Since the 'relatives' are statistically different from the 'healthy normal' control group at a level of $P < 0.000001$, some explanation will have to be sought and certainly much larger groups will have to be examined.

The utility of the malignin antigen and the antibody for general screening of populations for cancer is suggested by the low 'false positive' rates shown in FIG. 1 in the healthy normal and out-patient control groups. The results of the present studies also indicate, within the limitations of all laboratory procedures, that both the determination in cells of malignin and in serum of its antibody may be useful in helping to recognize the presence of malignant states in individuals in whom cancer is suspected. In addition, the clinical follow-up of individual patients over months and years has permitted the comparison of clinical outcome with antibody levels which were obtained on blind coded serum specimens. The correlation observed suggests that the anti-malignin antibody may be related to survival in that the elevated values during active disease were associated with longer survival and low levels during active disease with early death. After successful treatment, however, the presence of normal (low) antibody levels may be an aid in determining whether an active cancer state has been replaced by one in which there is 'no evidence of disease'. Once again, the laboratory value can have relevance only in relation to the clinical status, and it usually should not be difficult to separate the clinically healthy from the clinically terminal patient, both of whom have low levels of antibody, but for different reasons.

The significance of the correlation of lower levels of anti-malignin antibody with terminal illness shown in FIGS. 2A and 2B is not known. Since as seen in FIG. 2B, the drop in antibody can occur abruptly, in as little as one month before death, it is not known how many of the elevated values shown in FIG. 2A were followed by a similar drop prior to death. The drop may therefore be even more common than observed in the single determinations. The phenomeneon is in accord with previous demonstrations by others of the general decrease in immunocompetence observed to signal oncoming death in both human and animal cancer (15), and may simply represent a secondary consequence of the terminal state. However, since anti-malignin antibody is specific for a cancer cell antigen, localized preferentially in malignant cells in vitro and in vivo, and has been shown to be cytotoxic to malignant cells in vitro (7), the drop in antibody might be more central to the cancer process and be to the detriment of the patient. In addition, earlier data (6) showed anti-malignin antibody in human cancer sera to be largely 'disarmed', with its Fc portion cleaved from the Fab fragments, which would result in loss of cytotoxicity. This process might reflect one form of the cancer cell's defense against the antibody. The low levels of antibody observed here prior to death may be evidence of a second form of the cancer cell's defense, the result of increasing blockade of antibody production or release due to antigen excess as the tumor proliferates.

That malignin is not an 'onco-fetal' antigen is supported by the absence of malignin from fetal tissues. Malignin appears to be much older phylogenetically than those states commonly thought of as being recapitulated during fetal development; its only structural relatives, by computer search (16), are the ferredoxins of plants, *lucaena glauca* and alfalfa, the acyl carrier protein of *E. coli*, and cytochrome b5. These four share the property of being anaerobic enzymes, the ferredoxins being the most electro-negative oxidation-reduction enzymes in nature. Warburg observed the anaerobic advantage of malignant cells but was unable to account for this property in the activity of the then known anaerobic enzymes (17). The possibility that malignin is a cleaved derivative of such an anaerobic enzyme system, that this system is common to all malignancies regardless of cell type, and that this system imparts a unique anaerobic advantage to cancer cells, would be consistent with the demonstrated increase in the yield of malignin with increasing malignancy of cell growth (1,2), the ubiquity of distribution of the antigen, the cytotoxicity of the antibody and the antibody failure in the terminal state. Now that purified human anti-malignin antibody is available (6,7), and monoclonal anti-malignin antibodies are available, the therapeutic uses of the antibody acting alone or as a carrier for anti-cancer drugs can be further systematically examined.

REFERENCE FOR EXAMPLE 10A

1. Bogoch, S. Brain glycoproteins and recognition function: Recognins and cancer. Pages 555–556. In Volk, B. W. and Schneck, L. (eds), *Current Tends in Sphingolipidoses and Allied Disorders*, Plenum Press, New York, 1976.
2. Bogoch, S. Astrocytin and malignin: Two polypeptide fragments (recognins) related to brain tumor. *Nat. Cancer Inst. Mon.* 133–137, 1977.
3. Bogoch, S. The detection of malignant gliomas in brain by the quantitative production in vitro of TAG (target-attaching globulins) from human serum. Pp. 358–361. In Bogoch, S. (ed) *Biological Diagnosis of Brain Disorders*. Spectrum-Wiley Press, New York, 1974.
4. Bogoch, S. and Bogoch, E. S. Production of two recognins related to malignin: Recognin M from mammary MCF-7 carcinoma cells and recognin L from P$_3$J lymphoma cells. *Neurochemical Res.* 4: 465–472, 1979.
5. Bogoch, S., Bogoch, E. S., Fager, C., Goldensohn, E., Harris, J. H., Hickok, D. F., Lowden, J. A., Lux, W. E., Ransohoff, J., and Walker, M. D. Elevated anti-malignin antibody in the serum of cancer patients: A multi-hospital blind study. *Neurology* 29: 584, 1979.
6. Bogoch, S., and Bogoch, E. S. Disarmed anti-malignin antibody in human cancer. *Lancet*, 1, 987, 1979.
7. Bogoch, S. and Bogoch, E. S. Tumor markers: Malignin and related recognins associated with malignancy rather than with cell type. In Battistin, L., Hashim, G., and Lajtha, A. (eds) *Neurochemistry and Clinical Neurology*, pp. 407–424. Alan R. Liss, Inc., New York, 1980.
8. Rigby, P. The transforming genes of SV40 and polyoma viruses. *Nature* 282: 781–784, 1979.
9. Langan, T. Malignant transformation and protein phosphorylation. *Nature* 286: 329–330, 1980.
10. Krupey, J., Gold, P. and Freedman, S. O. Physicochemical studies of the carinoembryonic antigens of the human digestive system. *J. Exptl. Med.* 128: 387–398.
11. Bogoch, S. and Bogoch, E. S. Quantitative determination of anti-malignin antibody. In Rosenberg, S. A. (ed) *Serologic Analysis of Human Cancer Antigens*, pp. 693–696. Academic Press, Inc., New York, 1980.
12. Harris, J. H., Gohara, A., Redmond, F., Bogoch, S. and Bogoch, E. S. Immunofluorescent and serologic studies with anti-malignin antibody. In Rosenberg, S. A. (ed) *Serologic Analysis of Human Cancer Antigens*, pp. 571–582. Academic Press, Inc., New York, 1980.
13. Meck, R. A., Ingram, M., Meck, J. J., McCullough, J. L., Wu, M-C, and Yunis, A. A. Establishment and Cell Cycle Kinetics of a Human Squamous Cell Carcinoma in Nude Mice and in Vitro. *Cancer Res.* 4: 1076–1085, 1981.
14. Editorial, The Cancer Connection. *Lancet* 1: 635–636, 1977.
15. Hersh, E. M., Gutterman, J. U., Mavligit, G. M., Mountain, C. W., McBride, C. M., Burgess, M. A., Lurie, P. M., Zelen, M., Takita, H. and Vincent, R. G. Immunocompetence, Immunodeficiency and Prognosis in Cancer. *Ann. New York Acad. Sci.* 276: 386–406, 1976.
16. Dayhoff, M. O. (ed) *Atlas of Protein Sequence and Structure*. National Biomedical Reseach Foundation, Silver Spring, Md., 1972.
17. Warburg, O., Gaweh, K., Geissler, A. W., Schroder, W., Gewitz, H. S. and Volder, W. *Arch. Biochem. Biophys.* 78: 573, 1958.

EXAMPLE 11

Diagnosis of Tumor Cells by Immunofluorescence

The compounds Anti-Astrocytin, Anti-Malignin, and S-TAG have been shown to attach preferentially to tumor cells. This specificity permits use of these compounds to diagnose tumor cells in histology sections by conjugating dyes or radioactive substances to Anti-Astrocytin, Anti-Malignin, or S-TAG. Standard labeling techniques may then be used. A procedure using S-TAG is as follows.

One procedure which has been found satisfactory is a modified St. Marie procedure. Human brain tumor specimens are frozen and 5 micron thick sections cut. These are stored in a moist container at minus 70° C. for 4 to 8 weeks before staining. The conjugate may be a standard anti-serum such as goat anti-rabbit conjugate. The conjugate is labeled by techniques known in the art with fluoresein or other labeling substance. Fluorescein labeled goat anti-rabbit conjugate as commercially available may be used. The fluorescent technique used was a standard one in which a 1:200 to 1:400 solution of TAG is incubated for about 30 minutes or more on the tumor section, followed by washes to remove unattached TAG. Three washes with phosphate buffered saline has been found satisfactory. Conjugate incubation with fluorescein-labeled conjugate followed by washes is then performed, followed by microscopic inspection. Normal cells and their processes fail to stain both in tumor sections and in control sections of normal non-tumor brain. Fluorescence is brightly present in tumor glial cells and their processes.

EXAMPLE 11A

Detection of Non-Brain Malignant Cells with Fluorescent Signal From TAG

The uses of TAG products coupled with a signal emitter such as a dye or a radioactive label to detect cancer cells is described, for example, as indicated above and EXAMPLE 11 herein. In this EXAMPLE 11A, the detection of non-brain malignant cells is described.

As described in EXAMPLE 10 utilizing human serum in the determination of TAG, after the antimalignin antibody was bound to the immobilized antigen and non-bound serum proteins washed away, the antibody was cloven from the binding with 0.25 M acetic acid at 37° C. for 2 hours and the TARGET reagent separated from it by centrifugation. The TAG antibody solution was quantitated by means of its absorption at 280 mμ. The TAG solutions were stored at −20° C., then thawed and combined, brought to pH 7 by titration with 6N NaOH, dialyzed against phosphate buffered saline pH 7, filtered and concentrated on Millipore Pellicon 1000 membranes, centrifuged to clear insoluble protein and the immune globulin, complexes concentrated and freed of immunologically non-active compounds by Cellex D and Blue Sepharose CL6B (Pharmacia) chromatography. This human anti-malignin antibody reacts with anti-human gamma globulin in Ouchterlony double diffusion. When TAG is used with fluorescein conjugated to anti-human gamma globulin in standard double layer Coon immunofluorescence it stains malignant glia, breast carcinoma, ovarian carcinoma, adenocarcinoma of colon, and other types of cancer cells in postoperative and biopsy tissue sections, as well as in human sputum, bronchial washings, pleural effusion fluid, gastric aspirate and bladder urine. The concentration of protein in TAG which yield clear fluorescence when controls are negative, is 1 to 10 μg per section.

The production of a "purified" TAG was undertaken by reacting the sera from patients with a variety of cancers with bromoacetylcellulose-MALIGNIN by methods earlier described (EXAMPLE 8). The antibody bound in this reaction was cleaved with 0.25 M acetic acid, quantified by measurement at O.D. 280 using a conversion factor of 1.46 for gamma globulin frozen and stored at −20° C. This antibody was found to contain immunoglobulin as determined by anti-human gamma-globulin antiserum specific for gamma chains (BioRad Laboratories, Inc.) and with anti-FAB and anti-Fc fragments (Miles Laboratories). It also reacts with rabbit anti-human albumin (BioRad Laboratories).

It was found that whereas 10 to 50 micrograms of protein TAG are required to produce specific immunofluorescent staining of cells which contain Malignin, only 1 to 10 micrograms of purified protein TAG are required for this specific staining in all sections, and in a few, less than one microgram has been found to suffice.

It was found that the most active preparation of purified TAG is that which is eluted with the highest ionic strength elution, i.e., from 0.15 M to 1.5 M. Any method of production which uses this fact is useful; three preferred methods are given below.

Method I—Fractionation of TAG chromatography with DEAE cellulose (Cellex, D, BioRad Laboratories) was first employed with step-wise elution with increasing ionic strength and decreasing pH, the same sequence of eluants as that given in Example I for the production of Crude Astrocytin-Precursor-Containing Fraction. Good separation was obtained of the bulk of the protein into three fractions, Peak I obtained with Solution 1 (see Example 1) and Peak II obtained with Solution 1 (see Example 1) and Peak II obtained with Solution 6 and Solution 7. Ouchterlony double diffusion showed the TAG in Peak I still to contain appreciable protein with albumin mobility, and while Peak II contained most of the albumin, appreciable IgG could be detected. Rechromatography of Peak I gave a progressively pure IgG until, after the seventh chromatography, essentially no albumin (less than 3%) could be detected by Ouchterlony gel diffusion in which 5 to 10 micrograms of human albumin was detectable with rabbit anti-human albumin. The IgG so obtained was prone to denaturation and loss of immunological reactivity after a few days standing at −0°-5° C.

Method II—A second fractionation of TAG was made with chromatography on Sepharose CL-6B (Pharmacia, Inc.) starting with low molarity buffer (0.0005) and proceeding in two steps of 0.15 M and 1.5 M to elute the balance of the protein. As with the Cellex D, one passage was found to be inadequate to separate, and recycling slowly improved the product. Once again, the most active fraction vis-a-vis anti-malignin antibody was in the 1.5 M fractions.

Method III—Chromatography with Sepharose CL-6B next to the glass fritted disc and Cellex D layered above the Sepharose proved to be the most satisfactory method.

The graphical representation in FIG. 1 shows the fractions obtained on chromatography of TAG utilizing Method II. After the first eluate of 200 mls., 50 ml. or smaller sub-fractions were collected. The protein content of each eluate was determined by the optical density at 280 mμ with a uniform factor of 1.46 based on gamma globulin used to convert to micrograms for calculating recoveries. The absolute amount of protein requires correction in those fractions in which there is appreciable albumin. The points at which the stepwise solvent changes were made are indicated by arrows. The subfractions are designated by Roman numerals I through VIII.

The solvents corresponding to letters A-F at the arrows were as follows:
A—0.01 M TRIS (pH 7.2)
B—0.05 M TRIS with 0.1 M NaCl (pH 7.2)
C—PBS, 0.11 M CaCl (pH 7.2)
D—PBS, 0.165 M NaCl (pH 7.2)
E—PBS, 0.33 M NaCl (pH 7.2)
F—0.05 M TRIS, 1.5 M NaCl (pH 7.2)

In the following Table are shown the recoveries from each fraction, a semi-quantitative determination in each of the gamma-globulin and albumin in each, as well as the activity of each fraction in the immunofluorescent staining of cancer cells. (The plus sign indicates reaction, zero no reaction and plus/minus reaction in some cases).

TABLE

| Fraction | I | II | III | IV | V | VI | VII | VIII |
|---|---|---|---|---|---|---|---|---|
| Recovered | | | | | | | | |
| μg | 2,877 | 1,140 | 2,351 | 2,942 | 1,808 | 2,230 | 2,125 | 7,477 |
| % | 12.5 | 5.0 | 10.2 | 12.8 | 7.9 | 9.7 | 9.3 | 32.6 |
| Immunodiffusion Against: | | | | | | | | |
| Anti-human IgG specific for gamma chains | +++ | ++ | ++ | + | o | + | ++ | +++ |
| Anti-human albumin | + | + | + | ++ | +++ | +++ | +++ | +++ |
| Anti-Fab | + | ++ | o | ++ | + | o | ++ | ++ |
| Anti-Fc | ++ | ++ | + | ++ | + | o | + | o |
| Immunofluorescence | ± | ± | ± | ± | ± | ± | ± | +++ |

Photographs were prepared showing the line of reaction between anti-human gamma-globulin specific for gamma chains for each of Fractions I and VIII from above.

Photographs were taken showing the use of TAG (Fraction VIII from above) to stain non-brain malignant cells, i.e., a stain of bronchogenic carcinoma cells in the bronchial washings of a patient and a stain of lymphoma cells in the pleural fluid of a patient. Non-cancer cells do not fluoresce. The TAG (1 to 10 μg in 0.1 ml phosphate buffered saline (PBS) is applied to the surface of packed cells on a glass slide incubated 30 minutes, washed three times with PBS and then layered with fluorescein-conjugated anti-human IgG diluted until non-malignant control tissues give essentially no fluorescence. The cells are visualized with a Zeiss fluorescent microscope using a tungsten lamp and filters BG 23, BG 12, and 500.

EXAMPLE 12

BLIND STUDY OF TAG SPECIFICITY IN IMMUNOFLUORESCENCE

The presence of malignin was sought in cells collected from cancer patients and controls. Specimens were collected by thoracocentesis, paracentesis, bronchial or tracheal washings, sputum and pericardial effusion, from patients with lung, breast, prostatic, colon and undifferentiated cancers, as well as from non-cancer controls including patients with emphysema, heavy smoking and epilepsy; and sputum from a former cancer patient with no evidence of disease for two years following successful treatment. Cells were concentrated by centrifugation.

The following Table shows the correlation of presence or absence of malignin in cells as determined blind by immunofluorescent staining with anti-malignin antibody (TAG), and the clinical-pathological diagnosis. The TAG stain result was correct in 20/22 specimens (91%). Standard Papanicolaou stain examinations performed blind on duplicates of these specimens by other pathologists were correct in 17/22 specimens (77%).

| | | CELL MALIGNIN: IMMUNOFLUORESCENCE TAG RESULTS | | |
|---|---|---|---|---|
| | | cancer | non-cancer | total |
| Clinical-Pathological | Cancer | 14 | 2 | 16 |
| | Non-cancer | 0 | 6 | 6 |

| | | CELL MALIGNIN: IMMUNOFLUORESCENCE TAG RESULTS | | |
|---|---|---|---|---|
| | | cancer | non-cancer | total |
| Diagnosis | Total | 14 | 8 | 22 |

In addition to the positive stain for malignin cells from breast, ovarian and bronchogenic carcinoma, and astrocytomas, cells grown in tissue culture from human squamous cell carcinoma of the vulva, and from five different types of human lymphoma, as well as leukemic cells in both acute and chronic leukemia blood have demonstrated positive staining. Malignin was visualized and photographed in a variety of human cancer cells by anti-malignin antibody double-layer immunofluorescence. The second layer fluorescein-labelled anti-antibody was diluted in control experiments to as much as 1:1,600 until non-specific fluorescence was completely eliminated in the absence of the first layer anti-malignin antibody. Under these conditions, anti-malignin antibody was active at one nanogram anti-body protein per cancer cell in producing the specific immunofluorescence seen and photographed in: A—bronchogenic carcinoma cells, from bronchial washings; B—lymphocytic leukemia cell, from blood: C—ovarian carcinoma cells, at surgery; D—squamous cell carcinoma (2 cells), grown in tissue culture; E—astrocytoma, anaplastic, as surgery.

EXAMPLE 13

Detection of Cancer Cells with Radioisotope Signal From TAG

In this Example, the feasibility of attaching a radioactive label to TAG is demonstrated. Second, the injection into animals of this radio-labeled TAG has been accomplished and shown to be safe and effective. Third, the radio-labeled TAG localized preferentially in the cancer tissue when compared to normal tissue, thus indicating that the specificity previously demonstrated in vitro of the preference for cancer cells which is conveyed by the use of specific anti-Malignin TAG products in confirmed in vivo.

The Labeling of TAG with 99 m Technetium ($^{99m}Tc$)

Procedure for Labeling

1. Two preparations of TAG were used, here designated TAG-1 and TAG2. TAG-1 and TAG-2 (concentration of each 0.4 mg/0.5 ml) were added to separate sterile evacuated vials.

2. To each vial was added 0.1 ml of a stannous chloride solution (10 mg $SnCl_2 \cdot 2 H_2O$ in 100 ml of 0.01 N HCl). The vials were mixed for 3-4 minutes.

3. 0.1 ml. (6 mCi) of $^{99m}$Tc-pertechnetate (sodium salt) was added and mixed 2-3 minutes.

Procedure for determining labeling efficiency

Samples of the $^{99m}$Tc-TAG-1 and $^{99m}$Tc-TAG-2 were tested for labeling efficiency by descending paper chromatography using Watman No. 1 paper with 85% methanol as the solvent. A similar study was done with Sodium Pertechnetate-$^{99m}$Tc which acted as a control.

After 2 hours, the papers were removed from the chromatography tank and divided in two sections: (1) 1 cm about the origin; (2) the remaining paper up to the solvent front. Each section was then counted in a gamma well scintillation counter and its content of radioactivity determined (cpm).

Approximately 50 labda were plated on each paper strip.

Procedure for Antigen-Antibody Reaction

A portion of the labeled solution was also plated on an Ouchterlony gel plate to determine its ability to react with malignin in the antigen-antibody reaction. After a 3-hour period, the resulting sharp reactive lines were removed from the gel and their content of radioactivity measured. An equal portion of the gel not involved in the reaction was also removed and its content of radioactivity was also measured as background.

Results

Labeling Efficiency

TABLE 1

Labeling Efficiency of $^{99m}$Tc—TAG-1 and $^{99m}$Tc—TAG-2

| COMPOUND | SITE ON PAPER | CPM | % | CHEMICAL SPECIES |
|---|---|---|---|---|
| NaTcO$_4$—$^{99m}$Tc | origin | 4.94 × 10$^5$ | 7.33% | reduced TcO$_4$— |
| NaTcO$_4$—$^{99m}$Tc | solvent front | 6.25 × 10$^6$ | 92.67% | TcO$^4$— |
| TAG-1 | origin | 4.35 × 10$^6$ | 98.47% | TAG—$^{99m}$Tc |
| TAG-1 | solvent front | 6.76 × 10$^4$ | 1.53% | TcO$_4$— |
| TAG-2 | origin | 1.96 × 10$^6$ | 98.01% | TAG—$^{99m}$Tc |
| TAG-2 | solvent front | 3.98 × 10$^4$ | 1.99% | TcO$_4$— |

TABLE 2

ANTIGEN-ANTIBODY RESECTION

| GEL AREA | COUNTS PER MIN. | % |
|---|---|---|
| TAG-2 line | 1.99 × 10$^6$ | 92.04% |
| Background gel | 1.72 × 10$^5$ | 7.96% |

Conclusions

The following conclusions were reached relative to the quality control tests employed:

1. $^{99m}$Tc-pertechnetate was reduced by stannous chloride to a more reactive oxidation state (+4+5).
2. The reduced pertechnetate labeled both the TAG-1 and TAG-2 preparations.
3. The $^{99m}$Tc-TAG-2 was tested for its ability to retain its activity and was found to retain its ability to react immunologically.

The Use of Radio-Labeled TAG in vivo to Detect Cancer Cells

Wistar rats were injected intracerebrally with C6 glioma tumor cells which had had previous passages in rats and in tissue culture. The rats were observed for the first signs of growing tumor, such as weakness, tremor or unsteadiness. These symptons first appear seven to 10 days from injection, and with fast growing tumors result in death within three to four days in many animals, and one week in all. As soon as symptoms appeared, the animals were injected with labeled TAG intravenously in the tail vein, then the animal anesthetized at varying times, the brain removed, the tumor dissected from of normal brain, and the radioactivity in each dissected specimen compared.

| | Preliminary $^{99m}$Tc—TAG experiment | | | |
|---|---|---|---|---|
| Animal | Sacrifice (hr. post injection) | Tumor wt., mg. | Counts/gm./min. Tumor | Counts/gm./min. Normal Brain |
| A | 1.25 | 1.9 | 149,100 | 13,400 |
| B | 5.30 | 6.0 | 16,200 | 6,600 |
| C | 7.21 | 23.0 | 53,000 | 5,800 |
| D | 24.10 | 29.0 | 66,700 | 7.500 |

Tumor and normal brain specimens were counted overnight in the gamma-well counter. All samples and standards were decay corrected for convenience to the mid-count of the first sample in the sequence.

Conclusion

The preferential localization of radioactivity in tumor as compared to normal tissue is demonstrated above.

EXAMPLE 14

PRODUCTION OF MONOCLONAL ANTI-MALIGNIN ANTIBODIES, MAMA-S, MAMA-F, AND MAMA-FS, AND THEIR RESPECTIVE NOVEL PRODUCER CELLS

A myeloma cell line (P3×63-Ag-8) was cultured in Dulbecco's minimum essential medium supplemented with 10% fetal bovine serum (D$_{10}$), in a humidified incubator at 37° C. and 5% CO$_2$.

Inbred femal BALB/cJ mice (8 weeks of age) (Jackson Laboratory, Bar Harbor, Maine) were immunized intraperitoneally, 4 times at weekly intervals with Malignin emulsified in complete Freund's adjuvant (Difco). Sera of the immunized mice were tested for the presence of anti-malignin antibody and antibody positive mice were further boosted 4 days prior to cell fusion.

Immune spleen cells (10$^8$) were fused with the myeloma cell (10$^7$) using polyethylene glycol (PEG, 1000, J. T. Backer) as the fusion inducing agent as described by Galfre et al (Nature 266, 550-552, 1977). The PEG treated cell mix was seeded into 96 wells of a microtiter plate (Costar 3596) in D$_{10}$ supplemented with hypoxanthine, aminopterin, and thymidine (D$_{10}$ HAT) (Littlefield, J. W., Science 145: 709, 1964). About one half of D$_{10}$ HAT was replaced twice weekly for two weeks. The spleen cells did not survive in vitro, while the unfused myeloma cells were killed in D$_{10}$ HAT. Only the hybrid cells remained actively growing after 10 days under the selective conditions. After two weeks in D$_{10}$ HAT, the hybrid cells were fed with medium the same as D$_{10}$ HAT except with the omission of aminopterin (D$_{10}$ HT) for another week, then with D$_{10}$. Whenever the wells were about 80% covered by hybrid cells, supernatants were aspirated for anti-malignin antibody assay.

Cells from the antibody producing wells were cloned in soft agarose by modifications of the method as described by Cotton et al (Eur. J. Immunol. 3, 135–140, 1973). Briefly, an equal volume of warm 0.8% agarose (Seaplaque, Marine Colloid Inc.) and double strength $D_{10}$ were mixed and plated 2 ml to a 60 mm dish and chilled at 4° C. for 15 minutes as base layer. One thousand cells in the same medium were overlayered on the baselayer and chilled, then incubated in the same conditions as regular cell cultures. The anti-malignin antibody positive clones were further grown as ascitic tumors in BALB/cJ mice.

non-dialyzable and migrated on SDS-polyacrylamide gel electrophoresis predominately as gamma chain immunoglobulins.

With progressive recloning, each specific monoclonal antibody producing cell was concentrated. Thus, recloning of MAMA-B Producer Cells yielded four out of six colonies which were MAMA-B Producers, and recloning of MAMA-A Producer Cells yielded three out of four colonies which were MAMA-A Producers.

Each of the three types of antibody stained a wide range of malignate cells by immunofluorescence in approximately the same concentration range as previously observed with purified TAG products. That is, one nanogram of antibody protein stained one cancer cell. Photographs were taken of specific immunofluorescent

TABLE - EXAMPLE 14

Quantity of Antibody (μg/ml extracellular fluid) for Each
(F = fast reacting, in 10 minutes;
S = slow reacting, in 2 hours;
F/S = both types of antibody produced; Method as in EXAMPLE 10)

| Extra-Cellular Fluid | Months After Manufacture of PRODUCER CELLS | MAMA-F | | MAMA-S | | MAMA-F/S | |
|---|---|---|---|---|---|---|---|
| Cell Supernate | 1 mo. | 38 | 32 | 22 | 27 | 21 | 25/21 |
| | | 67 | 32 | 38 | 37 | 27 | 21/21 |
| | | 19 | 42 | 27 | 53 | 21 | 21/19 |
| | | 27 | 30 | 55 | 62 | 25 | 25/23 |
| | | 25 | 21 | 27 | 32 | 23 | 29/27 |
| | | 26 | 29 | 37 | 26 | 44 | 48/45 |
| | | 52 | 23 | 29 | 34 | 33 | 2/18 |
| | | | | | | 30 | |
| Cell Supernate | 3 mo. | 51 | | 16 | | 41/34 | 41/39 |
| | | 136 | | 15 | | 36/36 | 29/23 |
| | | 73 | | 16 | | 47/41 | 39/37 |
| | | 44 | | 29 | | 39/33 | 30/27 |
| | | 32 | | | | 62/58 | 22/22 |
| | | 30 | | | | 101/110 | 15/18 |
| | | 23 | | | | 30/29 | 18/18 |
| Cell Supernate | 4 mo. | 19 | 30 | 18 | 18 | 30/34 | 32/29 |
| | | 32 | 30 | 26 | 23 | 15/16 | 21/23 |
| | | 30 | 27 | 25 | 27 | 27/26 | 23/21 |
| | | 27 | | 29 | 30 | | |
| | | | | 30 | 29 | | |
| Cell Supernate | 5 mo. | 126 | 140 | 34 | 88 | 47/97 | 49/82 |
| | | 178 | 393 | 248 | 69 | 22/27 | 74/178 |
| | | 162 | 296 | 89 | 114 | 26/30 | 83/149 |
| | | | | 92 | 123 | 56/127 94/232 | |
| | | | | | | 308/82 | 112/79 |
| | | | | | | 62/107 | 56/169 |
| | | | | | | 164/390 | 178/164 |
| | | | | | | 249/301 | |
| Mouse Ascites Fluid | 8 mo. | | | | | 660/1,070 | |
| | | | | | | 780/670 | |

The above Table shows the quantities of monoclonal anti-malignin antibody produced by each antibody producing clone, in micrograms of protein per ml of extracellular fluid. The yields of antibody are seen to be good for the first four months of propagation of the clones, and to have increased by the fifth month of propagation. The cells continued to grow well through the eighth month and to successfully grow when transferred intraperitoneally to the mouse, where the yield of antibody again increased as expected to as much as 1 mg. of MAMA-S per ml of ascites fluid. The cells also grew successfully on soft agar and where frozen and stored in liquid nitrogen and grown again after thawing. Aliquots of each clone where frozen in liquid nitrogen for permanent storage and regrowth at later dates.

The monoclonal anitbody in each case was quantified as protein by optical density at 280 millimicrons, was staining obtained with human leukemic blood, both acute and chronic, six cultured lined of leukemia cells (JY, KARPAS, CEM, RAJI, HL60, and K562), and three human lymphomas. Staining was obtained with MAMA-F, MAMA-S and MAMA-FS.

Second layer staining with fluorsecent labels, both fluorescein and rhodamine, at concentrations as low as 1:1,600 was observed and recorded. These very low concentrations of the second layer permitted dilution until background non-specific staining was eliminated, and at those concentrations of second layer (FITC or rhodamine) highly specific staining was obtained with MAMA-F, MAMA-S and MAMA FS.

EXAMPLE 15

DEMONSTRATION BY CYTOFLUOROGRAPHY OF A DIAGNOSTIC "MALIGNIN FLUORESCENT INDEX" WITH MONOCLONAL ANTI-MALIGNIN ANTIBODIES F and S Using the two monoclonal anti-malignin antibodies, MAMA-F and MAMA-S, in several concentrations, time of incubation, washing or no washing, different concentrations and time of incubation of fluorescein isothiocyanate anti-mouse antibody (FITC), and other specifications as to method of preparing blood and/or white cells, in both normal and cancer sera (leukemias, lymphomas), in a study of how these antibodies may best be used with flow cytometry instruments, the following conclusions and preferred examples are discussed:

1. By quantitating the actual number of cells fluorescing per 100 cells counted and correcting for the cells fluorescing without MAMA but with the FITC antibody alone, an absolute number is obtained which represents the true or specific fluorescence due to MAMA. Thus, Malignin Fluorescent Index = (Number of Cells fluorescing with MAMA plus FITC) less (Number of cells fluorescing with FITC alone)

2. The Malignin Fluorescent Index is a rapid diagnostic test for malignant cells in fluid suspension, which distinguishes normal from malignant cells regardless of the cell type (malignin is a general transformation antigen which relates to the process of malignant transformation rather than the cell type).
3. Examples from the data obtained:

chamber, usually arranged to contain about 100 live cells, is counted. These cells are then treated with the agent being tested and the number of cells which are still alive is counted.

In a standard test of cytotoxicity of S-TAG Solution obtained in accordance with the methods of EXAMPLE 9 against cells in tissue culture derived from a patient with a glioblastoma Grade III–IV, well characterized as of glial origin, S-TAG produced death of all cells in the counting chamber even when in high dilution of 1:00 and 1:1000, representing as little as 0.2 and 0.02 µg of S-TAG per ml. of solution. Similar results are obtained with high dilutions of Anti-Astrocytin and Anti-Malignin.

Both the specificity exhibited in EXAMPLES 11, 11A, 12, 13, 14 and 15 and the cytotoxicity demonstrated in this EXAMPLE and EXAMPLE 17 are highly relevant to the therapeutic possibilities of Anti-Astrocytin, Anti-Malignin and S-TAG for malignant tumors in man. The practical diagnostic potential of both of these phenomena for tumor tissue removed at operation but requiring diagnosis by histology is already demonstrated herein.

EXAMPLE 17

DEMONSTRATION OF CYTOTOXICITY OF A MIXTURE OF MONOCLONAL ANTI-MALIGNIN ANTIBODIES MAMA-F AND MAMA-S

Whereas either MAMA-F or MAMA-S alone do not produce appreciable cytotoxicity with malignant cells, when these two monoclonal antibodies are mixed, the mixture is actively cytotoxic to malignant cells. In addition, the product MAMA-FS is cytotoxic. All three

| Date + Specimen | MAMA Used | Time, min. | Washed +/− | FITC min. | Cells fluorescing/100 (corrected) | | | Specific Total | Malignin Fluorescent Index |
|---|---|---|---|---|---|---|---|---|---|
| | | | | | Region 2 | Region 3 | Region 4 | | |
| 4/29/81 | | | | | | | | | |
| Normal | 0 | 20 | 0 | 30 | 4.1 | 13.3 | 36.5 | | |
| Normal | MAMA-F | 20 | 0 | 30 | 3.5 | 12.3 | 31.7 | | |
| | specific | | | | −0.6 | −1.0 | −4.8 | −6.4 | |
| Leukemia (L) | 0 | 20 | 0 | 30 | 11.8 | 7.8 | 3.0 | | |
| Leukemia (L) (Acute) | MAMA-F specific | 20 | 0 | 30 | 15.4 | 7.8 | 3.2 | | |
| | | | | | +3.6 | 0 | +0.2 | +3.8 | |
| | | | | | | | | | +10.2 |
| 4/29/81 | | | | | | | | | |
| Normal | 0 vs. MAMA-S | 60 | + | 10 | −5.4 | −0.2 | +1.6 | −4.0 | |
| Leukemia (L) | 0 vs. MAMA-S | 60 | + | 10 | +0.8 | +0.3 | −0.2 | +1.3 | +5.3 |
| Leukemia (VH) Chronic | 0 vs. MAMA-S | 60 | + | 10 | −2.7 | −14.1 | +0.5 | −16.3 | −12.3 |
| Lymphoma (S10) | 0 vs. MAMA-S | 60 | + | 10 | +0.1 | +0.4 | +11.8 | +12.3 | +16.3 |
| Lymphoma (S15) | 0 vs. MAMA-S | 60 | + | 10 | −0.5 | −0.3 | +6.1 | +5.3 | +9.3 |
| Lymphoma (S16) | 0 vs. MAMA-S | 60 | + | 10 | −0.5 | −0.2 | +4.5 | +3.8 | +7.8 |

EXAMPLE 16

Demonstration that Anti-Astrocytin, Anti-Malignin and S-TAG are Cytotoxic to Tumor Cells Growing in Tissue Culture.

Standard tests for determinging cytotoxicity may be used. Generally, the number of cells in a fixed counting preparations are cytotoxic in approximately the same concentrations as previously observed for Anti-Astrocytin, Anti-Malignin and S-TAG products (EXAMPLE 16). Approximately one nanogram of antibody per cell is cytotoxic, resulting in lysis of the cell.

Cytotoxicity also was observed and recorded on both the Coulter cytofluorograph and on the Ortho cytofluorograph, each of which permits absolute counts of viable cells with time. Destruction of viable malignant cells (carcinoma of the pancreas, leukemic and lymphoma) was observed over a period of 15 to 60 minutes. Those malignant cells which were identified by light scatter and specifically by fluorescence were destroyed by either the mixture of MAMA-F and MAMA-S or by MAMA-FS. The killing of cancer cells is, by definition, a therapeutic process, and the products which produce this killing, are by definition, therapeutic products.

What is claimed is:

1. A process for detecting the presence of cancerous or malignant tumor cells in a cell collection, said cells comprising a cancer RECOGNIN, comprising applying to said cell collection a specific monoclonal anti-cancer RECOGNIN antibody, which attaches to cancerous cells and can thereby be detected by visible or signal-emitting means attached to said antibody, said cancer RECOGNIN being derived from cancerous tumor tissue or cells, and characterized by forming a single line precipitate with its specific antibody in quantitative precipitin tests and Ouchterlony gel diffusion tests, being soluble in water and aqueous solutions having an acid or neutral pH, and insoluble at alkaline pH, having a spectrophotometric absorption peak wave length of 280 m$\mu$ and a molecular weight of from about 3,000 to about 25,000, and further characterized by having an amino acid residue composition characterized by high proportions of glutamic and aspartic acids and high ratios of glutamic and aspartic acids to histidine.

2. The process according to claim 1 wherein said cell collection is in vivo.

3. The process according to claim 1 wherein said cell collection is in vitro.

4. The process according to claim 1 wherein the cancer RECOGNIN is MALIGNIN.

5. A composition comprising monoclonal anti-MALIGNIN antibody-FAST or a purified fraction thereof, whereby said antibody or a purified fraction thereof attaches to cancerous cells, said cells comprising MALIGNIN; and can thereby be detected by visible or signal-emitting means attached to said antibody, said MALIGNIN being derived from brain tumor cells, and which forms a single line precipitate with its specific antibody in quantitative precipitin tests and Ouchterlony gel diffusion tests, being soluble in water and aqueous solution having an acid or neutral pH, and insoluble at an alkaline pH, and has a spectrophotometric absorption peak wave length of 280$\mu$, a molecular weight of about 10,000, and an amino acid composition approximately as follows:

|  | APPROXIMATE NO. OF RESIDUES |
| --- | --- |
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| ½ Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
|  | 89 | ammonia and the amino acids cysteic, hydroxyproline, norleucine, isodesmosine, lysinonorleucine and gamma-aminobutyric acid being absent in detectable amounts.

6. A composition comprising monoclonal anti-MALIGNIN antibody-SLOW or a purified fraction thereof, whereby said antibody or a purified fraction thereof attaches to cancerous cells, said cells comprising MALIGNIN; and can thereby be detected by visible or signal-emitting means attached to said antibody, said MALIGNIN being derived from brain tumor cells, and which forms a single line precipitate with its specific antibody in quantitative precipitin tests and Ouchterlony gel diffusion tests, being soluble in water and aqueous solution having an acid or neutral pH, and insoluble at an alkaline pH, and has a spectrophotometric absorption peak wave length of 280 m$\mu$, a molecular weight of about 10,000, and an amino acid composition approximately as follows:

|  | APPROXIMATE NO. OF RESIDUES |
| --- | --- |
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| ½ Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
|  | 89 | ammonia and the amino acids cysteic, hydroxyproline, norleucine, isodesmosine, lysinonorleucine and gamma-aminobutyric acid being absent in detectable amounts.

7. A composition comprising monoclonal anti-MALIGNIN antibody-FAST and SLOW or a purified fraction thereof, whereby said antibody is cytotoxic to and kills said cancer cells, said cells comprising MALIGNIN, whereby said antibody or a purified fraction thereof attaches to cancerous cells and can thereby to detected by visible or signal-emitting means attached to said antibody, said MALIGNIN being derived from brain tumor cells, and which forms a single line precipitate with its specific antibody in quantitive precipitin tests and Ouchterlony gel diffusion tests, being soluble in water and aqueous solution having an acid or neutral pH, and insoluble at a alkaline pH, and has an spectrophotometric absorption peak wave length of 280 m$\mu$, a molecular weight of about 10,000, and an amino acid composition approximately as follows:

| | APPROXIMATE NO. OF RESIDUES |
|---|---|
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| ½ Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| | 89 | ammonia and the amino acids cysteic, hydroxyproline, norleucine, isodesmosine, lysinonorleucine and gamma-aminobutyric acid being absent in detectable amounts.

8. A composition comprising a mixture of the antibody according to claim 5, monoclonal anti-MALIGNIN antibody-FAST or a purified fraction thereof and the antibody according to claim 6, monoclonal anti-MALIGNIN antibody-SLOW or a purified fraction thereof, whereby said mixture is cytotoxic to and kills cancerous cells.

9. The product according to claim 5 wherein said monoclonal anti-MALIGNIN antibody-FAST is complexed with any substance which it is desired to have preferentially attached to cancerous cells.

10. The product according to claim 6 wherein said monoclonal anti-MALIGNIN antibody-SLOW is complexed with any substance which it is desired to have preferentially attached to cancerous cells.

11. The product according to claim 7 wherein said monoclonal anti-MALIGNIN antibody-FAST/SLOW is complexed with any substance which it is desired to have preferentially attached to cancer cells.

12. A composition comprising monoclonal anti-cancer RECOGNIN antibody whereby said anti-cancer RECOGNIN antibody is produced by the injection into an organism or collection of cells of a purified cancer RECOGNIN said cancer RECOGNIN having the ability to induce or cause the cells of said organism or collection to produce specific anti-cancer RECOGNIN antibody, wherein such anti-cancer RECOGNIN antibody producing cells are treated to make them self-perpetuating and identified by their production of monoclonal anti-cancer RECOGNIN antibody, said cancer RECOGNIN being derived from cancerous tumor tissue or cells, and characterized by forming a single line precipitate with its specific antibody in quantitative precipitin tests and Ouchterlony gel diffusion tests, being soluble in water and aqueous solutions having an acid or neutral pH, and insoluble at alkaline pH, having a spectrophotometric absorption peak wave length of 280 m$\mu$ and a molecular weight of from about 3,000 to about 25,000, and further characterized by having an amino acid residue composition characterized by high proportions of glutamic and aspartic acids and high ratios of glutamic and aspartic acids to histidine.

13. The product according to claim 12 comprising a monoclonal anti-cancer RECOGNIN antibody or a purified fraction thereof which is cytotoxic to and kills cancerous cells.

14. The composition according to claim 12 further comprising a complex of said monoclonal anti-cancer RECOGNIN antibody or a purified fraction thereof and any substance which it is desired to have attached to cancerous cells.

15. The composition according to claim 12 further comprising visible or signal-emitting means attached to said antibody or a purified fraction thereof whereby cancer cells are detectable by said means when said antibody is attached to said cells.

16. The composition of claim 12 wherein said antibody-producing cells are hybridized to make them self-perpetuating.

17. The composition of claim 16 wherein said cells are the cells of a murine organism.

18. The process according to claim 1 wherein said antibody or antibody fraction is derived by a process comprising priming antibody-producing cells with a purified cancer RECOGNIN.

19. The process according to claim 18 wherein said antibody is hybridomally produced by a process comprising priming murine spleen cells with a purified cancer RECOGNIN.

20. The composition of claims 5, 6 or 7 wherein said antibody or antibody fraction is derived by a process comprising priming antibody-producing cells with purified MALIGNIN.

21. The composition of claim 20 wherein said antibody or antibody fraction is hybridomally-produced by a process comprising priming murine spleen cells.

* * * * *